(12) United States Patent
Miller et al.

(10) Patent No.: US 10,369,133 B2
(45) Date of Patent: Aug. 6, 2019

(54) IMMUNOSUPPRESSIVE COMPOUNDS AND THERAPEUTICS

(71) Applicants: UNIVERSITY OF TENNESSEE RESEARCH FOUNDATION, Memphis, TN (US); RXBIO, INC., Johnson City, TN (US)

(72) Inventors: Duane Douglas Miller, Collierville, TN (US); Charles Ryan Yates, Collierville, TN (US); Jayaprakash Pagadala, Parkland, FL (US); Ram Mahato, Omaha, NE (US); Hao Wu, Shanghai (CN)

(73) Assignee: THE UNIVERSITY OF TENNESSEE RESEARCH FOUNDATION, Memphis, TN (US)

( * ) Notice: Subject to any disclaimer, the term of this patent is extended or adjusted under 35 U.S.C. 154(b) by 0 days.

(21) Appl. No.: 14/907,015

(22) PCT Filed: Jul. 23, 2014

(86) PCT No.: PCT/US2014/047845
§ 371 (c)(1),
(2) Date: Jan. 22, 2016

(87) PCT Pub. No.: WO2015/013422
PCT Pub. Date: Jan. 29, 2015

(65) Prior Publication Data
US 2016/0175281 A1 Jun. 23, 2016

Related U.S. Application Data

(60) Provisional application No. 61/857,664, filed on Jul. 23, 2013.

(51) Int. Cl.
*A61P 37/06* (2006.01)
*A61K 31/343* (2006.01)
*A61K 31/365* (2006.01)
*A61K 31/661* (2006.01)
*A61K 31/665* (2006.01)

(52) U.S. Cl.
CPC .......... *A61K 31/365* (2013.01); *A61K 31/343* (2013.01); *A61K 31/661* (2013.01); *A61K 31/665* (2013.01); *A61P 37/06* (2018.01)

(58) Field of Classification Search
CPC .............................. A61K 31/665; A61P 37/06
USPC ........................................................ 514/100
See application file for complete search history.

(56) References Cited

U.S. PATENT DOCUMENTS

| 4,868,153 A | 9/1989 | Allison et al. |
| 2008/0171724 A1 | 7/2008 | Watkins et al. |
| 2009/0234015 A1 | 9/2009 | Yates et al. |
| 2012/0283331 A1 | 11/2012 | Yates et al. |

FOREIGN PATENT DOCUMENTS

WO 2009062200 A1 5/2009

OTHER PUBLICATIONS

Wu, H. Gene Therapy and Stem Cell Therapy to Improve the Outcome of Human Islet Transplantation, Dissertation, The University of Tennessee Health Science Center. May 2013.
Wu. H et al. Synthesis and Characterization of an Anti-Apoptotic Immunosuppressive Compound for Improving the Outcome of Islet Transplantion, Bioconjugate Chemistry, Nov. 20, 2013m vol. 24, pp. 2036-2044.
Zeng, K et al. Synthesis and biological evaluation of quinic acid derivatives as anti-inflammatory agents, Bioorganic and Medicinal Chemistry Letters, 2009, vol. 19, pp. 5458-5460.
International Search Report and Written Opinion for PCT/US14/47845.

*Primary Examiner* — Kevin E Weddington
(74) *Attorney, Agent, or Firm* — Lihua Zheng

(57) ABSTRACT

Here provided are new immunosuppressive compounds and novel therapeutics for improving tissue transplantation.

15 Claims, 22 Drawing Sheets

| Flow Phase | Flow rate | Detection |
|---|---|---|
| ACN:water=50:50 | 1.0mL/min | UV@240nm |

Figure 9C

| Flow Phase | Flow rate | Detection |
|---|---|---|
| ACN:water=50:50 | 0.5mL/min | UV@240nm |

IMMUNOSUPPRESSIVE COMPOUNDS AND THERAPEUTICS

CROSS-REFERENCE TO RELATED APPLICATIONS

This application is a U.S. national phase application of PCT/US2014/47845, filed Jul. 23, 2014, which claims priority to U.S. Provisional Patent Application Nos. 61/857,664 filed on Jul. 23, 2013, the disclosure of which applications are incorporated herein by reference.

GOVERNMENTAL SUPPORT

The invention was made with funding from the United States National Institutes of Health (NIH) RO1 DK69968 and NIH5R33AI080534-05. The U.S. government may have certain rights in the invention.

FIELD OF INVENTION

The invention relates to new immunosuppressive compounds and methods of use of the compounds for improving survival and function in transplanted cells and organs. More specifically, the new compounds can improve islet cell transplantation.

BACKGROUND

Clinical islet transplantation presents significant challenges and much research has been directed to improving its outcome. More than 500 patients with type 1 diabetes have received human islet transplantation worldwide and demonstrated improved quality-of-life afterwards. However, the wide application of human islet transplantation is still hindered by two major barriers, the limited supply of donor islets and inadequate means to prevent immune rejection of the transplanted cells. Immune rejection is a common cause of graft failure after islet transplantation. Although immunosuppressive drugs such as tacrolimus, sirolimus and mycophenolic acid (MPA) can prevent immune rejection in many cases, these drugs also impair insulin release from transplanted human islets and long-term injections of these drugs may cause loss-of-function in human islet cells, a status characterized as the primary non-function (PNF). Besides the immunosuppressive drugs, PNF can also be caused by inflammatory cytokines, the hypoxic environment and reactive oxygen species.

MPA is a commonly used immunosuppressive drug in human islet transplantation. MPA inhibits inosine 5'-monophosphate dehydrogenase (IMPDH), an essential enzyme mediating purine synthesis in T cells and B cells. MPA also induces down-regulation of anti-apoptotic factors such as B-cell lymphoma 2 (Bcl-2) and B-cell lymphoma-extra-large (Bcl-xL), and an accumulation of pro-apoptotic mediators such as caspase-3 and small mitochondria-derived activator of caspases (SMACs), suggesting that MPA may impair islet function through the activation of the apoptotic pathway in human islet cells.

It is desirable to develop a new immunosuppressive compound with less side effects and a therapy thereof for improving the outcome of cell and/or organ transplantation.

SUMMARY OF THE INVENTION

In one aspect, the invention is directed to a method for improving survival and function of a transplanted tissue, by administering to the tissue a therapeutically-effective amount of mycophenolic acid or its derivative or pro-drug thereof, and a compound of Formula I:

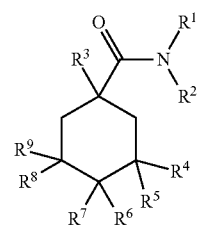

(I)

In Formula I, the ring may be singly, doubly, or completely saturated. In Formula I, $R^1$, $R^2$, $R^3$, $R^4$, $R^5$, $R^6$, $R^7$, $R^8$, and $R^9$ are each independently selected from the group consisting of: H or OH; a straight- and branched-chain alkyl having one to twelve carbon atoms; an alkylidene that is a divalent radical having one to twelve carbon atoms; an alkenyl that is straight- and branched-chain alkenyl groups having from two to twelve carbon atoms; an alkynyl that is straight- and branched-chain alkynyl groups having from two to twelve carbon atoms; a cycloalkyl that is saturated or partially unsaturated carbocycles having from three to twelve carbon atoms, including bicyclic and tricyclic cycloalkyl structures; a heterocycloalkyl that is a saturated or partially unsaturated monocyclic radical containing carbon atoms, preferably with 4 or 5 ring carbon atoms, and with at least one heteroatom selected from nitrogen, oxygen (e.g., monosaccharide) and sulfur; an aryl or heteroaryl that have monocyclic and polycyclic unsaturated or aromatic ring structures, with "aryl" referring to those that are carbocycles and "heteroaryl" referring to those that are heterocycles; an alkoxy that is a radical —O-alkyl; an aryloxy; a cycloalkoxyl; an alkylthio; an alkylamino; an arylthio; an acylamino; a cycloalkylthio; a cycloalkylamino; a heteroarylthio; a heteroarylamino; and a halogen.

In some embodiments, every member in each group of Formula I may be taken independently or combined via covalent bond in any order with some or all members of any group defined above to the extent that these combinations give rise to chemically feasible entities; and each of the groups 'b' through 's' may contain or be substituted by any one or more functional groups taken from the functional group pool listed below either singularly, in plurality or in combination with other members of the functional group, which functional group pool is consisting of ether, thioether, amine, nitro, nitrile, sulfoxides, sulfones, ester, amide, hydroxamic acid, sulfonamides, sulfamide, ureas, sulfimines, sulfonylureas, carbamates, thiocarbamates, carbonates and hydroxyl.

In some embodiments, the alkyl in Formula I may be selected from the group consisting of methyl (Me), ethyl (Et), n-propyl, isopropyl, butyl, isobutyl, sec-butyl, tert-butyl (t-Bu), pentyl, isopentyl, tert-pentyl, hexyl, and isohexyl. In other embodiments, the alkyl may be an alkyl having from 1 to 8 carbon atoms. In still other embodiments, the alkyl may be a substituted alkyl selected from the group consisting of fluoromethyl, difluoromethyl, trifluoromethyl, 2-fluoroethyl, 3-fluoropropyl, hydroxymethyl, 2-hydroxyethyl, and 3-hydroxypropyl.

In some embodiments, the alkylidene in Formula I may be selected from the group consisting of $CH_2$, $CHCH_3$, and $(CH_3)_2$. In other embodiments, the alkenyl of Formula I may be selected from the group consisting of prop-2-enyl, but-3-enyl, hex-3-enyl, 2-methylprop-2-enyl, and hept-2-enyl.

In some embodiments, the cycloalkyl in Formula I may be selected from the group consisting of cyclopropyl, cyclobutyl, cyclopentyl, cyclohexyl, and cycloheptyl. In other embodiments, the aromatic ring structures in the aryl or heteroaryl may be selected from the group consisting of phenyl, naphthyl, 1,2,3,4-tetrahydronaphthyl, furyl, thienyl, pyrrolyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and a fused-ring structure or bridge, for example, $OCH_2$.

In some embodiments, the alkoxy in Formula I may be selected from the group consisting of methoxy, ethoxy, and propoxy. In other embodiments, the halogen may be selected from the group consisting of chlorine, fluorine, bromine and iodine.

In another aspect, the present invention is directed to a method for improving survival and function of a transplanted tissue, comprising administering to the tissue a therapeutically-effective amount of a compound of Formula II or Formula III:

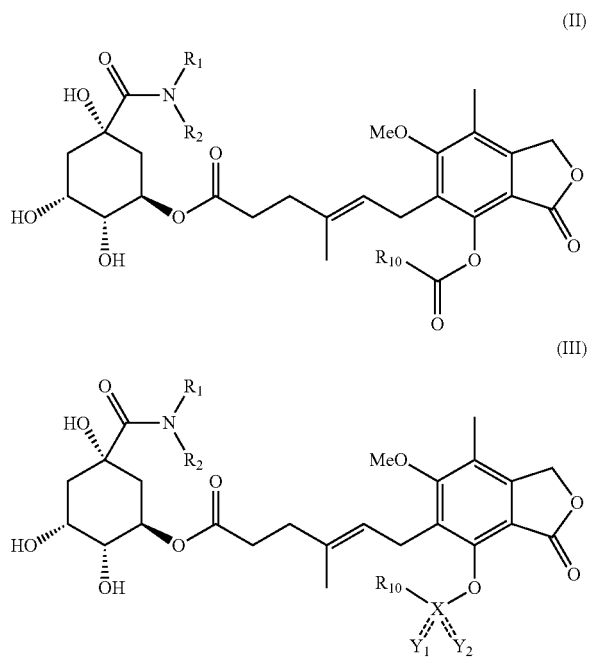

In some embodiments, the X in Formula III may be S or P. In some embodiments, $Y_1$ and $Y_2$ in Formula III are each independently O or N.

In some embodiments, $R_1$, $R_2$ and $R_{10}$ in Formulas II and III are each selected from the group consisting of: H or OH; a straight- and branched-chain alkyl having one to twelve carbon atoms; an alkylidene that is a divalent radical having one to twelve carbon atoms; an alkenyl that is straight- and branched-chain alkenyl groups having from two to twelve carbon atoms; an alkynyl that is straight- and branched-chain alkynyl groups having from two to twelve carbon atoms; a cycloalkyl that is saturated or partially unsaturated carbocycles having from three to twelve carbon atoms, including bicyclic and tricyclic cycloalkyl structures; a heterocycloalkyl that is a saturated or partially unsaturated monocyclic radical containing carbon atoms, preferably with 4 or 5 ring carbon atoms, and with at least one heteroatom selected from nitrogen, oxygen (e.g., monosaccharide) and sulfur; an aryl or heteroaryl that have monocyclic and polycyclic unsaturated or aromatic ring structures, with "aryl" referring to those that are carbocycles and "heteroaryl" referring to those that are heterocycles; an alkoxy that is a radical —O-alkyl; an aryloxy; a cycloalkoxyl; an alkylthio; an alkylamino; an arylthio; an arylamino; a cycloalkylthio; a cycloalkylamino; a heteroarylthio; a heteroarylamino; and a halogen.

In some embodiments, every member in each group of Formulas II and III may be taken independently or combined via covalent bond in any order with some or all members of any group defined above to the extent that these combinations give rise to chemically feasible entities; and each of the groups 'b' through 's' may contain or be substituted by any one or more functional groups taken from the functional group pool listed below either singularly, in plurality or in combination with other members of the functional group, which functional group pool is consisting of ether, thioether, amine, nitro, nitrile, sulfoxides, sulfones, ester, amide, hydroxamic acid, sulfonamides, sulfamide, ureas, sulfimines, sulfonylureas, carbamates, thiocarbamates, carbonates and hydroxyl.

In some embodiments, the alkyl in Formulas II and III may be selected from the group consisting of methyl (Me), ethyl (Et), n-propyl, isopropyl, butyl, isobutyl, sec-butyl, tert-butyl (t-Bu), pentyl, isopentyl, tert-pentyl, hexyl, and isohexyl. In other embodiments, the alkyl may be an alkyl having from 1 to 8 carbon atoms. In still other embodiments, the alkyl may be a substituted alkyl selected from the group consisting of fluoromethyl, difluoromethyl, trifluoromethyl, 2-fluoroethyl, 3-fluoropropyl, hydroxymethyl, 2-hydroxyethyl, and 3-hydroxypropyl.

In some embodiments, the alkylidene in Formulas II and III may be selected from the group consisting of $CH_2$, $CHCH_3$, and $(CH_3)_2$. In other embodiments, the alkenyl of Formulas II and III may be selected from the group consisting of prop-2-enyl, but-3-enyl, hex-3-enyl, 2-methylprop-2-enyl, and hept-2-enyl.

In some embodiments, the cycloalkyl in Formulas II and III may be selected from the group consisting of cyclopropyl, cyclobutyl, cyclopentyl, cyclohexyl, and cycloheptyl. In other embodiments, the aromatic ring structures in the aryl or heteroaryl may be selected from the group consisting of phenyl, naphthyl, 1,2,3,4-tetrahydronaphthyl, furyl, thienyl, pyrrolyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and a fused-ring structure or bridge, for example, $OCH_2$.

In some embodiments, the alkoxy in Formulas II and III may be selected from the group consisting of methoxy, ethoxy, and propoxy. In other embodiments, the halogen may be selected from the group consisting of chlorine, fluorine, bromine and iodine.

In some embodiments of the above methods, the compound of Formula II is a compound of Formula IV (IV)

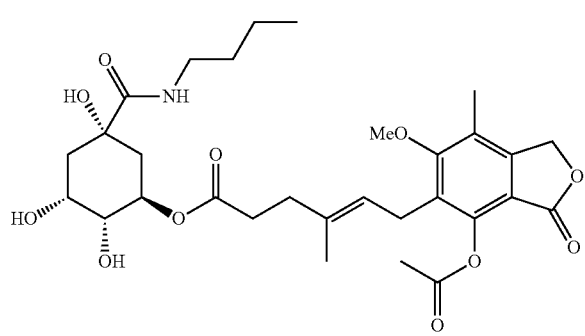

In some embodiments of the above methods, the compound of Formula III is a compound of Formula V (V)

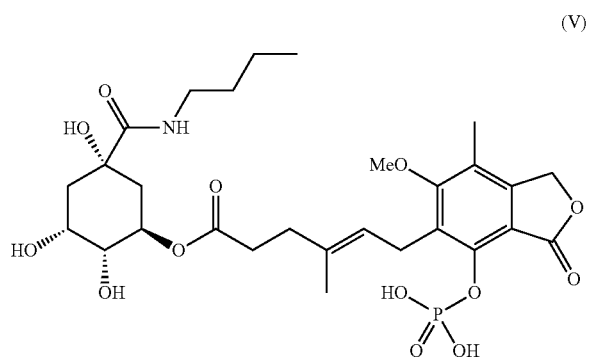

In some further embodiments, the methods comprise a further step of administering a therapeutically-effective amount of a compound of Formula I.

In still another aspect, the present invention is directed to a compound or a pharmaceutically acceptable salt form thereof according to Formulas II, III, IV or V.

In still further aspect, the present invention is directed to a pharmaceutical composition comprising the compound or the pharmaceutically acceptable salt form thereof according to Formulas II, III, IV or V.

BRIEF DESCRIPTION OF THE DRAWINGS

FIG. 7A shows a chart depicting the HPLC conditions. The column was Inertsil ODS-3, 250×4.6 mm, 5 μm.

FIG. 9C shows the HPLC settings.

DETAILED DESCRIPTION OF THE INVENTION

Figure 1:
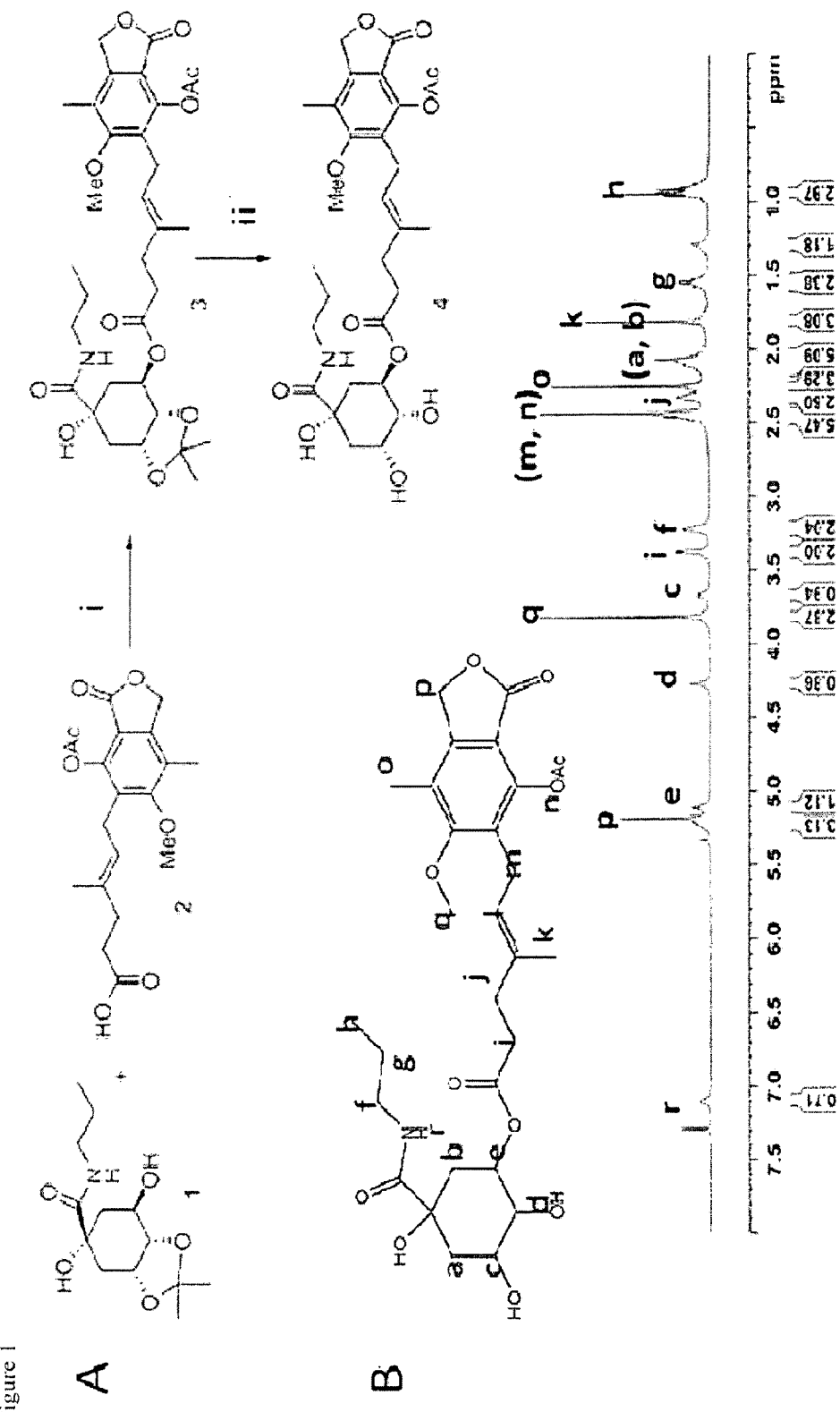
FIG. 1A shows the synthesis scheme of JP-3-110 (aka, compound of formula IV). Condition (i) refers to DIC, DMAP, DCM, 73%; ii) IN HCl/THF, 12 h, 21%.
FIG. 1B shows the 1H NMR spectrum of JP-3-110.

The present invention is partly based on a newly synthesized compound and the surprising discovery that the new compounds have unexpected traits in improving cell or tissue transplantation. The present invention is also partly based on the surprising discovery of a new combination therapy in improving cell or tissue transplantation. Some of the discoveries are also described in a scientific publication at *Bioconjug Chem.* 2013 Dec. 18; 24(12):2036-44. Epub 2013 Nov. 27, which is incorporated herein by reference in its entirety.

The inventors were able to create (1R,2R,3R,5S)-5-(butylcarbamoyl)-2,3,5-trihydroxycyclohexyl (E)-6-(4-acetoxy-6-methoxy-7-methyl-3-oxo-1,3-dihydroisobenzofuran-5-yl)-4-methylhex-4-enoate (herein named "JP-3-110") by conjugating TNP and MPA via ester bond and establish the safety and effectiveness of this new compound drug in inhibiting the alloreactivity of human peripheral blood mononuclear cells (PBMCs) and to promote human islet cell insulin release. The inventors also established that the concurrent administration of TNP and MPA given as individual compounds has similar effects.

In one aspect, the invention is directed to a method for improving survival and function of transplanted cells, tissues and/or organs (which will collectively be referred to herein as "tissue" or "tissues"), by administering to a tissue for transplant a therapeutically-effective amount of mycophenolic acid and a compound of Formula I:

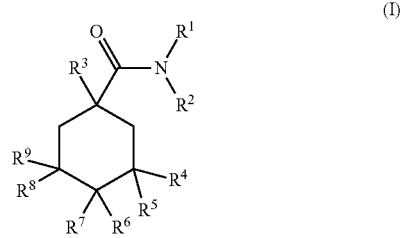

(I)

In Formula I, the ring may be singly, doubly, or completely saturated, and $R_1$, $R_2$, $R_3$, $R_4$, $R_5$, $R_6$, $R_7$, $R_8$, and $R_9$ are each selected from the groups listed below.

The groups may include H or OH; a straight- and branched-chain alkyl having one to twelve carbon atoms; an alkylidene that is a divalent radical having one to twelve carbon atoms; an alkenyl that is straight- and branched-chain alkenyl groups having from two to twelve carbon atoms; an alkynyl that is straight- and branched-chain alkynyl groups having from two to twelve carbon atoms; a cycloalkyl that is saturated or partially unsaturated carbocycles having from three to twelve carbon atoms, including bicyclic and tricyclic cycloalkyl structures; a heterocycloalkyl that is a saturated or partially unsaturated monocyclic radical containing carbon atoms, preferably with 4 or 5 ring carbon atoms, and with at least one heteroatom selected from nitrogen, oxygen (e.g., monosaccharide) and sulfur; an aryl or heteroaryl that have monocyclic and polycyclic unsaturated or aromatic ring structures, with "aryl" referring to those that are carbocycles and "heteroaryl" referring to those that are heterocycles; an alkoxy that is a radical —O-alkyl; an aryloxy; a cycloalkoxyl; an alkylthio; an alkylamino; an arylthio; an arylamino; a cycloalkylthio; a cycloalkylamino; a heteroarylthio; a heteroarylamino; and a halogen.

In some embodiments of Formula I, every member in each group may be taken independently or combined via covalent bond in any order with some or all members of any group defined above to the extent that these combinations give rise to chemically feasible entities; and each of the groups 'b' through 's' may contain or be substituted by any one or more functional groups taken from the functional group pool listed below either singularly, in plurality or in combination with other members of the functional group, which functional group pool is consisting of Ether, thioether, amine, nitro, nitrile, sulfoxides, sulfones, ester, amide, hydroxamic acid, sulfonamides, sulfamide, ureas, sulfimines, sulfonylureas, carbamates, thiocarbamates, carbonates and hydroxyl.

In some embodiments, the alkyl in Formula I may be selected from the group consisting of methyl (Me), ethyl (Et), n-propyl, isopropyl, butyl, isobutyl, sec-butyl, tert-butyl (t-Bu), pentyl, isopentyl, tert-pentyl, hexyl, and isohexyl. In other embodiments, the alkyl may be an alkyl having from 1 to 8 carbon atoms. In still other embodiments, the alkyl may be a substituted alkyl selected from the group consisting of fluoromethyl, difluoromethyl, trifluoromethyl, 2-fluoroethyl, 3-fluoropropyl, hydroxymethyl, 2-hydroxyethyl, and 3-hydroxypropyl.

In some embodiments, the alkylidene in Formula I may be selected from the group consisting of $CH_2$, $CHCH_3$, and $(CH_3)_2$. In other embodiments, the alkenyl of Formula I may be selected from the group consisting of prop-2-enyl, but-3-enyl, hex-3-enyl, 2-methylprop-2-enyl, and hept-2-enyl.

In some embodiments, the cycloalkyl in Formula I may be selected from the group consisting of cyclopropyl, cyclobutyl, cyclopentyl, cyclohexyl, and cycloheptyl. In other embodiments, the aromatic ring structures in the aryl or heteroaryl may be selected from the group consisting of phenyl, naphthyl, 1,2,3,4-tetrahydronaphthyl, furyl, thienyl, pyrrolyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and a fused-ring structure or bridge, for example, $OCH_2$.

In some embodiments, the alkoxy in Formula I may be selected from the group consisting of methoxy, ethoxy, and propoxy. In other embodiments, the halogen may be selected from the group consisting of chlorine, fluorine, bromine and iodine.

The terms "comprising" and "including" are used in an open, non-limiting sense.

In another aspect, the invention is directed to a method for improving survival and function of transplanted cells and/or organs, by administering to a tissue for transplant a therapeutically-effective amount of Formula II, III, IV, or V.

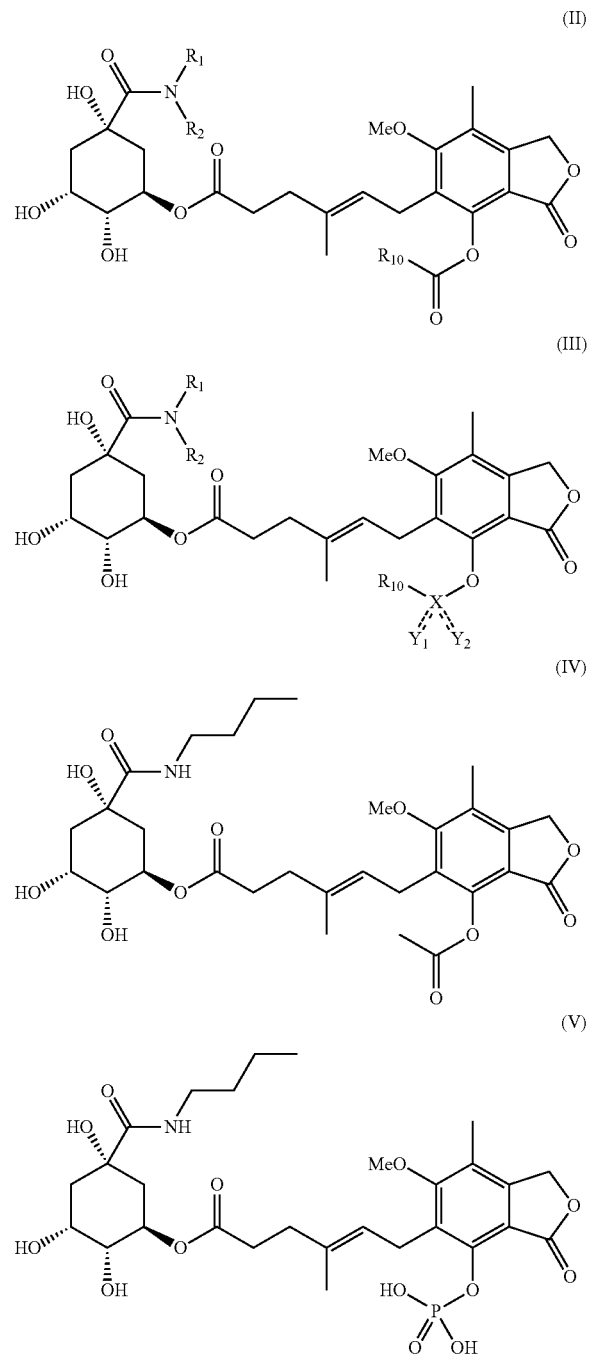

In some embodiments, the X is Formula III may be S or P. In some embodiments, $Y_1$ and $Y_2$ in Formula III are each independently O or N.

In some embodiments, $R_1$, $R_2$ and $R_{10}$ in Formulas II and III are each selected from the group consisting of: H or OH; a straight- and branched-chain alkyl having one to twelve carbon atoms; an alkylidene that is a divalent radical having one to twelve carbon atoms; an alkenyl that is straight- and branched-chain alkenyl groups having from two to twelve carbon atoms; an alkynyl that is straight- and branched-chain alkynyl groups having from two to twelve carbon atoms; a cycloalkyl that is saturated or partially unsaturated carbocycles having from three to twelve carbon atoms, including bicyclic and tricyclic cycloalkyl structures; a heterocycloalkyl that is a saturated or partially unsaturated monocyclic radical containing carbon atoms, preferably with 4 or 5 ring carbon atoms, and with at least one heteroatom selected from nitrogen, oxygen (e.g., monosaccharide) and sulfur; an aryl or heteroaryl that have monocyclic and polycyclic unsaturated or aromatic ring structures, with "aryl" referring to those that are carbocycles and "heteroaryl" referring to those that are heterocycles; an alkoxy that is a radical —O-alkyl; an aryloxy; a cycloalkoxyl; an alkylthio; an alkylamino; an arylthio; an arylamino; a cycloalkylthio; a cycloalkylamino; a heteroarylthio; a heteroarylamino; and a halogen.

In some embodiments of Formulas II and III, every member in each group may be taken independently or combined via covalent bond in any order with some or all members of any group defined above to the extent that these combinations give rise to chemically feasible entities; and each of the groups 'b' through 's' may contain or be substituted by any one or more functional groups taken from the functional group pool listed below either singularly, in plurality or in combination with other members of the functional group, which functional group pool is consisting of Ether, thioether, amine, nitro, nitrile, sulfoxides, sulfones, ester, amide, hydroxamic acid, sulfonamides, sulfamide, ureas, sulfimines, sulfonylureas, carbamates, thiocarbamates, carbonates and hydroxyl.

In some embodiments, the alkyl in Formulas II and III may be selected from the group consisting of methyl (Me), ethyl (Et), n-propyl, isopropyl, butyl, isobutyl, sec-butyl, tert-butyl (t-Bu), pentyl, isopentyl, tert-pentyl, hexyl, and isohexyl. In other embodiments, the alkyl may be an alkyl having from 1 to 8 carbon atoms. In still other embodiments, the alkyl may be a substituted alkyl selected from the group consisting of fluoromethyl, difluoromethyl, trifluoromethyl, 2-fluoroethyl, 3-fluoropropyl, hydroxymethyl, 2-hydroxyethyl, and 3-hydroxypropyl.

In some embodiments, the alkylidene in Formulas II and III may be selected from the group consisting of $CH_2$, $CHCH_3$, and $(CH_3)_2$. In other embodiments, the alkenyl of Formulas II and III may be selected from the group consisting of prop-2-enyl, but-3-enyl, hex-3-enyl, 2-methylprop-2-enyl, and hept-2-enyl.

In some embodiments, the cycloalkyl in Formulas II and III may be selected from the group consisting of cyclopropyl, cyclobutyl, cyclopentyl, cyclohexyl, and cycloheptyl. In other embodiments, the aromatic ring structures in the aryl or heteroaryl may be selected from the group consisting of phenyl, naphthyl, 1,2,3,4-tetrahydronaphthyl, furyl, thienyl, pyrrolyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and a fused-ring structure or bridge, for example, $OCH_2$.

In some embodiments, the alkoxy in Formulas II and III may be selected from the group consisting of methoxy, ethoxy, and propoxy. In other embodiments, the halogen may be selected from the group consisting of chlorine, fluorine, bromine and iodine.

In another aspect, the invention is directed to a compound of Formulas II, III, IV or V.

Some of the inventive compounds of Formulas II, III, IV or V may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as well as unsolvated forms of the identified structures. For example, all anticipated compounds include compounds of the indicated or expected structure in both hydrated and non-hydrated forms. Other examples of solvates include the structures in combination with isopropanol, ethanol, methanol, DMSO, ethyl acetate, acetic acid, or ethanolamine.

In addition to the novel inhibitors described above, the invention includes pharmaceutically acceptable prodrugs, pharmaceutically active metabolites, and pharmaceutically acceptable salts of such compounds.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. All are incorporated herein by reference. See, e.g., Bertolini et al., J. Med. Chem., 40: 2011-2016 (1997); Shan et al., J. Pharm. Sci., 86 (7): 765-767 (1997) Bagshawe, D7 ug Dev. Res., 34: 220-230 (1995); Bodor, Advances in Drug Res., 13: 224-331 (1984); Bundgaard, "Design of Prodrugs" (Elsevier Press, 1985); Larsen, Design and Application of Prodrugs, Drug Design and Development (Krogsgaard-Larsen et al. eds., Harwood Academic Publishers, 1991); Dear et al., Chromatogr. B, 748: 281-293 (2000); Spraul et al., J. Pharmaceutical & Biomedical Analysis, 10 (8): 601-605 (1992); and Prox et al., Xenobiol, 3 (2): 103-112 (1992).

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, .gamma.-hydroxybutyrates, glycollates, tartrates, methane-sulfonates, propanesulfonates, naphthalene-1-sulfonates, naphthalene-2-sulfonates, and mandelates.

If the compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

In some embodiments, therapeutically effective amounts of the agents of the invention may be used to improve survival and function of transplanted cells and/or organs, the method comprising of administering to a tissue for transplant a therapeutically-effective amount of mycophenolic acid and a compound of Formula I.

In other embodiments, therapeutically effective amounts of the agents of the invention may be used to improve survival and function of transplanted cells and/or organs, the method comprising of administering to a tissue for transplant a therapeutically-effective amount of Formulas II and III. The compounds in Formulas II and III could also be administered to a mammal in need of the required therapy.

An "therapeutically effective amount" is intended to mean that amount of an agent that, when administered to the tissue or a mammal in need of such treatment, is sufficient to effect treatment to improve survival and function of transplanted cells and/or organs. Thus, for example, a therapeutically effective amount of a compound from this invention, salt, active metabolite or prodrug thereof is a quantity sufficient to modulate and/or regulate survival and function of the transplanted cells and/or organs.

The amount of a given agent that will correspond to such an amount may vary depending upon factors such as the particular compound, tissue or organ that is targeted, the mammal being treated in addition factors e.g., weight of the mammal in need of treatment, but assessment of a therapeutically effective amount is well within the skill of one in the medical and pharmaceutical arts, given the disclosure herein. For example, the U.S. Department of Health and Human Services Food and Drug Administration Center for Drug Evaluation and Research (CDER) has established guidance for estimating dosages (*Guidance for Industry: Estimating the Maximum Safe Starting Dose in Initial Clinical Trials for Therapeutics in Adult Healthy Volunteers*, July 2005).

Therapeutically effective doses may be achieved via administration of a single dose, but may also be achieved via administration of more than one dose, such as an initial dose in combination with one or more additional doses which may be provided within a specific timeframe, for example, such as within about 12 to about 72 hours after the initial dose.

"Treating" is intended to mean at least the mitigation or stabilization for the benefit of survival of the tissue or organ or mammal. Therapy may be continued as needed to ensure survival of the tissue or organ or mammal or the therapy may be instated prior to or during transplant of tissue or organ to either the tissue or organ or even the mammal prior to actual tissue or organ transplantation.

The inventive agents may be prepared using the chemical knowledge and employing the techniques available to those trained in the art using starting materials that are readily available.

In some embodiments, the compound of Formula I-V may be administered in a pharmaceutical composition containing the compound in combination with other chemical components such as physiologically suitable carriers and excipients in order to facilitate administration of the compound to a target site. Such pharmaceutical compositions can be prepared by methods and contain excipients which are well known in the art. Such methods and ingredients may be found in Remington's Pharmaceutical Sciences (Alfonso Gennaro et al., eds., Lippincott, Williams & Wilkins, Baltimore, Md., 20th ed., 2000).

For example, a pharmaceutically acceptable carrier may be a carrier, an adjuvant or a diluent that does not cause significant irritation to an organism and does not abrogate the biological activity and properties of the administered compound. An excipient may be an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Proper formulation of compounds is dependent upon the route of administration chosen. Suitable routes of systematic administration of the compound may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections. Alternately, one may administer the compound in a local rather than systemic manner, for example, via injection of the pharmaceutical composition directly into a tissue region of a patient, for example, the eye.

The compounds may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It should be understood that this invention is not limited to the particular methodologies, protocols and reagents, described herein, which may vary. The terminology used herein is for the purpose of describing particular embodiments only, and is not intended to limit the scope of the present invention.

Examples of the disclosed subject matter are set forth below. Other features, objects, and advantages of the disclosed subject matter will be apparent from the detailed description, figures, examples and claims. Methods and materials substantially similar or equivalent to those described herein can be used in the practice or testing of the presently disclosed subject matter. Exemplary methods and materials are now described as follows.

EXAMPLES

Materials

Rat insulinoma INS-1E cell is a kind gift from Professor Claes B. Wolheim (University Medical Center, Geneva, Switzerland). Human islets were received from Integrated Islet Distribution Program (Duarte, Calif.). CMRL-1066 medium for islet culture and DAPI were purchased from Sigma Aldrich (St. Louis, Mo.). FBS was purchased from MediaTech Cellgro. (Herndon, Va.). PBS was purchased from GIBCO-BRL (Gaithersburg, Md.). NF-κB SEAPorter™ Assay Kit was purchased from IMGENEX (San Diego, Calif.). Human IL-2, IL-2sRa, IL-10 ELISA, TNFα and IFN-γ ELISA kits were purchased from R&D Systems (Minneapolis, Minn.). The primary antibodies for CD3, CD4, insulin and the Dylight 488-conjugated secondary antibody were purchased from Abcam (Cambridge, Mass.). The Alexa Fluor 568-conjugated secondary antibody and 0.25% trypsin were purchased from Invitrogen (Carlsbad, Calif.). Ultrasensitive One Touch glucose test strips and One Touch Ultra glucometer were purchased from LifeScan (Milpitas, Calif.). Tissue-Tek O.C.T. compounds were purchased from Sakura Finetek (Torrance, Calif.).

Synthesis and Characterization of Antiapoptotic Immunosuppressive Drug

The synthetic scheme is shown in FIG. 1A. All reagents for the synthesis were purchased from commercial sources and were used without further purification. Moisture-sensitive reactions were carried out under an argon atmosphere. Routine TLC was performed on aluminum backed Uniplates (Analtech, Newark, Del.). NMR spectra were obtained on a Bruker ARX-400 MHz (Billerica, Mass.) or a Varian Inova-500 MHz spectrometer (Varian NMR Inc., Palo Alto, Calif.). Chemical shifts are reported as parts per million (ppm) relative to TMS (0 ppm) in $CDCl_3$. Temperature was regulated with a general accuracy of $\pm 0.1°$ C. Mass spectral data were collected on a Bruker ESQUIRE-LC/MS system equipped with an ESI source. The synthesis of ester 4 used in the pancreatic islets protection studies was synthesized as illustrated in FIG. 1A. The starting compound 5,7-dihydroxy-2,2-dimethyl-N-propyl-hexahydrobenzo[d][1,3]dioxole-5-carboxamide (amide 1), which has been described before (see Zeng et al., 2012. Anti-inflammatory quinic acid derivatives for oral administration, United States) was coupled with acetylated MPA 2 to obtain quinic acid ester 3 and further deprotection of acetanoid group using 1N HCl in tetrahydrofuran (THF) to give compound 4.

Synthesis of Compound 2. Acetic anhydride (0.2 mL, 1.9 mmol) was slowly added to a pyridine (5 mL) solution of MPA (0.2 g, 0.62 mmol) and 4-Dimethylaminopyridine (DMAP, 0.03 g, 0.25 mmol) at 0° C. The reaction mixture was stirred for 2 h and then poured onto crushed ice. The aqueous phase was acidified with 2 M aq. HCl (pH~2) and extracted with EtOAc (3×400 mL). The combined organic extracts were dried over $Na_2SO_4$, filtered, and the solvent was removed under reduced pressure to afford acetylated MPA 2 (0.18 g, 83%) as a white powder mp 155-157° C. 1H NMR (500 MHz, $CDCl_3$): δ 5.18-5.5 (m, 3H), 3.79 (s, 3H), 3.28 (d, J=6.9 Hz, 2 H), 2.43-2.38 (m, 5H), 2.33-2.28 (m, 2H), 2.21 (s, 3H), 1.79 (s, 3H). Mass: 385.2 (M+Na).

Synthesis of Compound 3. A solution of amide 1 (0.32 g, 0.88 mmol), acetylated MPA 2 (0.24 g, 0.88 mmol), N,N-dimethyl amino pyridine (0.16 g, 1.32 mmol) and diisopropyl carbodiimide (0.21 mL, 1.32 mmol) in $CH_2Cl_2$ (10 mL) was stirred at room temperature under Ar atmosphere overnight. The reaction mixture was diluted with $CHCl_3$ (20 mL) and then washed with 1 N HCl (10 mL), water (10 mL), aqueous saturated $NaHCO_3$ solution (10 mL), and brine (10 mL). The organic layer was dried ($Na_2SO_4$) and evaporated, and the residue was purified by column chromatography (silica gel, 30% acetone in petroleum ether) to afford (E)-6-hydroxy-2,2-dimethyl-6-(propylcarbamoyl)-hexahydrobenzo[d][1,3]dioxol-4-yl-6-(4-acetoxy-6-methoxy-7-methyl-3-oxo-1,3-dihydroisobenzofuran-5-yl)-4-methylhex-4-enoate (compound 3, 0.4 g, 73%) as a white solid mp 71-73° C. 1H NMR (400 MHz, $CDCl_3$): δ 7.08 (t, 1 H), 5.32-5.23 (m, 1H), 5.17 (s, 1H), 5.15-5.08 (m, 1H), 5.32-5.24 (m, 1H), 4.54-0.48 (m, 1H), 4.14-4.08 (m, 1H), 3.84 (s, 1H), 3.78 (s, 3H), 3.5 (d, J=6.9 Hz, 2 H), 3.24-3.15 (m, 2H), 2.45-2.36 (m, 5H), 2.33-2.28 (m, 2H), 2.23 (s, 3H), 2.03-1.90 (m, 2H), 1.76 (s, 3H), 1.58 (s, 3H), 1.55-1.48 (m, 2H), 1.36 (s, 3H). 0.93 (t, 3H). Mass: 640.3 (M+Na).

Synthesis of Compound 4. Compound 3 (0.4 g, 0.64 mmol) was dissolved in THF (3 mL), then aqueous 1N HCl (5 mL) was added at room temperature and the reaction mixture was stirred for 12 h and monitored by ESI-MS. After completion of reaction, solution was saturated with solid NaCl and aqueous phase was extracted with ethyl acetate (3×100 mL). The organic layer was dried ($Na_2SO_4$) and evaporated, and the residue was purified by column chromatography (silica gel, 90% ethyl acetate in petroleum ether) to afford compound 4 (0.08 g, 21%) as a white solid mp 74-76° C. 1H NMR (400 MHz, $CDCl_3$): δ 7.08 (t, 1 H), 5.22-5.16 (m, 3H), 5.11-5.05 (m, 1H), 4.84 (s, 1H), 4.29-4.24 (m, 1H), 3.80 (s, 3H), 3.68-3.61 (m, 1H), 3.38 (d, J=6.9 Hz, 2 H), 3.32-3.30 (M, 1H), 3.25-3.16 (m, 3H), 2.45-2.36 (m, 5H), 2.33-2.28 (m, 2H), 2.23 (s, 3H), 2.15-2.0 (m, 4H), 1.8 (s, 3H), 1.51-1.50 (m, 2H), 0.9 (t, 3H). Mass: 578.3 (M+H).

NF-κB Activity

INS-1E cells which were stably transfected with the SEAP gene containing the response-element for NF-κB were used to screen for anti-inflammatory activity. Briefly, $10^6$ cells/well were seeded overnight followed by treatment with 10 ng/mL human recombinant TNFα and either TNP or hybrid drug JP-3-110 (1 μM). SEAP activity was measured 18 h later in supernatant samples (50 IL) using the NF-κB SEAPorter™ Assay Kit (IMGENEX, San Diego, Calif.) and a microplate luminometer. SEAP activity was normalized to the total protein content. Inhibitory potency (IC50) was determined from dose-response curves (n=3 separate experiments).

Apoptosis Studies

A cytokine cocktail (5 ng/ml TNFα and 5 ng/ml IL-1β) was used to mimic the in vivo challenge to the INS-1E cells and human islets by the inflammatory cytokines. Caspase-Glo 3 assay kits were used to analyze caspase 3 as per the manufacturer's protocol (Promega, Madison, Wis.). This assay kit provides a proilluminescent caspase substrate, DEVD, that, when cleaved by caspases, will release luciferin to quantitatively determine caspase concentration. Briefly, following sequential treatment by JP-3-110 for 48 h and a cytokine cocktail of recombinant for additional 48 h, 100 μL of Caspase-Glo reagent was added to 100 μL of culture supernatants in 96-well plates and incubated at room temperature for 1 h. The contents were then transferred into culture tubes, and luminescence was determined using a luminometer (Berthold, Germany).

The apoptosis of INS-1E cells was analyzed using terminal deoxynucleotidyl transferase dUTP nick end labeling (TUNEL). Briefly, following JP-3-110 treatment for 48 h and cytokine cocktail treatment for additional 48 h, INS-1E cells were characterized by the DeadEnd™ Colorimetric TUNEL system (Promega, Madison, Wis., USA), in which fragmented DNA from apoptotic cells was labeled with biotinylated nucleotide and detected using hydrogen peroxide and diaminobenzidine. For human islets, following treatment with JP-3-110 and cytokines, human islets were digested with 0.25% trypsin/EDTA into a single-cell suspension, stained with the Annexin V-FITC Apoptosis Detection Kit (Abcam, Cambridge, Mass.) and analyzed with flow cytometry. Annexin V binds to phosphatidylserine on the cell surface, which is a feature found in apoptotic cells. Fluorescent intensity was analyzed using CellQuest software (BD Bioscience, Franklin Lakes, N.J.). Three sets of independent transduction experiments were carried out for each assay.

Insulin Release

A static incubation method was used to evaluate the function of INS-1E cells as described before. See Wu et al., 2010, *Molecular pharmaceutics*, 7:1655-1666. Briefly, after transduction media was carefully removed with pipette, INS-1E cells and human islets were sequentially incubated in the media containing basal (1.67 mM) and stimulatory glucose (16.7 mM) at 37° C. for 1 h. Supernatants were collected and analyzed for insulin release by Insulin Ultrasensitive EIA kit (Alpco Diagnostics, Salem, N.H.). Insulin secretion was expressed as μIU/ml and the ratio of insulin levels at stimulatory glucose to basal glucose was used to calculate the stimulation index.

The insulin secretion from human islets was quantified using a dynamic islet perifusion assay as described before.

See Wu et al., 2011, *The Journal of Gene Medicine*, 13:658-669. Briefly, 50 islets from each group were handpicked and loaded onto a Swinnex 13 chamber (Millipore, Burlington, Mass., USA) and perifused with Krebs-Ringer bicarbonate HEPES buffer of the following composition (in mM): 129 NaCl, 5 NaHCO$_3$, 4.8 KCl, 1.2 KH$_2$PO$_4$, 1.2 MgSO$_4$, 2.5 CaCl$_2$, and 10 HEPES at pH 7.4. The flow rate was maintained at 1 ml/min with a peristaltic pump (Themo Fisher, Waltham, Mass.) and the temperature was maintained at 37° C. with a solution heater (Warner Instruments, Hamden, Conn.). Islets were first perifused with basal glucose for 60 min, stimulatory glucose for 20 min and basal glucose until insulin release reversed to the basal level. The perifusion speed was set to 2 mL/minute and samples were collected once per minute through an automatic fraction collector (Waters, Milford, Mass.) and analyzed for insulin content by ELISA.

Mixed Lymphocyte Reaction (MLR)

PBMCs were isolated using Ficoll Paque. T cells were isolated from PBMCs using Dynabeads for. T cells were stimulated with PHA (1 µg/ml) for 24 h alone or in the presence of TNP (5 µM) or JP-3-110 (5 µM) for additional 4 days. The total number of PBMCs was measured using T4 Automatic Cell Counter (Nexcelom, Lawrence, Mass.). The extent of T cell activation was determined by measuring the level of IL-2, IL-2sRa, TNFα and IFN-γ in the medium using ELISA at indicated time.

Humanized NSG Mice

Human PBMCs were isolated from buffy coats by gradient centrifugation using Ficoll Paque. The T cells and B cells of PBMCs were stained with FITC conjugated CD3 antibody and APC conjugated CD19 antibody, respectively, and characterized using flow cytometry. The PBMCs were infused into diabetic NSG mice at the concentration of 5×106/mouse to establish human immunity. The settlement of T cells in the spleen was assessed by immunofluorescence staining. Briefly, spleen were isolated, washed with PBS, fixed in 4% paraformaldehyde overnight, and embedded in optimal cutting temperature compound. Frozen sections of 5 µm thickness were cut. The slides were stained with rabbit anti-human CD3 primary antibody (1:200) at 4° C. overnight and Alexa Fluor 568 conjugated goat anti-rabbit secondary antibody (1:500) at room temperature for 1 h. The function of B cells was assessed by measuring human IgG concentration in the mouse blood.

Statistical Analysis

Statistical significance of the difference between the two groups was determined by unpaired t-test and between several groups by one-way ANOVA.

Results

Synthesis and Characterization of JP-3-110

Figure 9A:
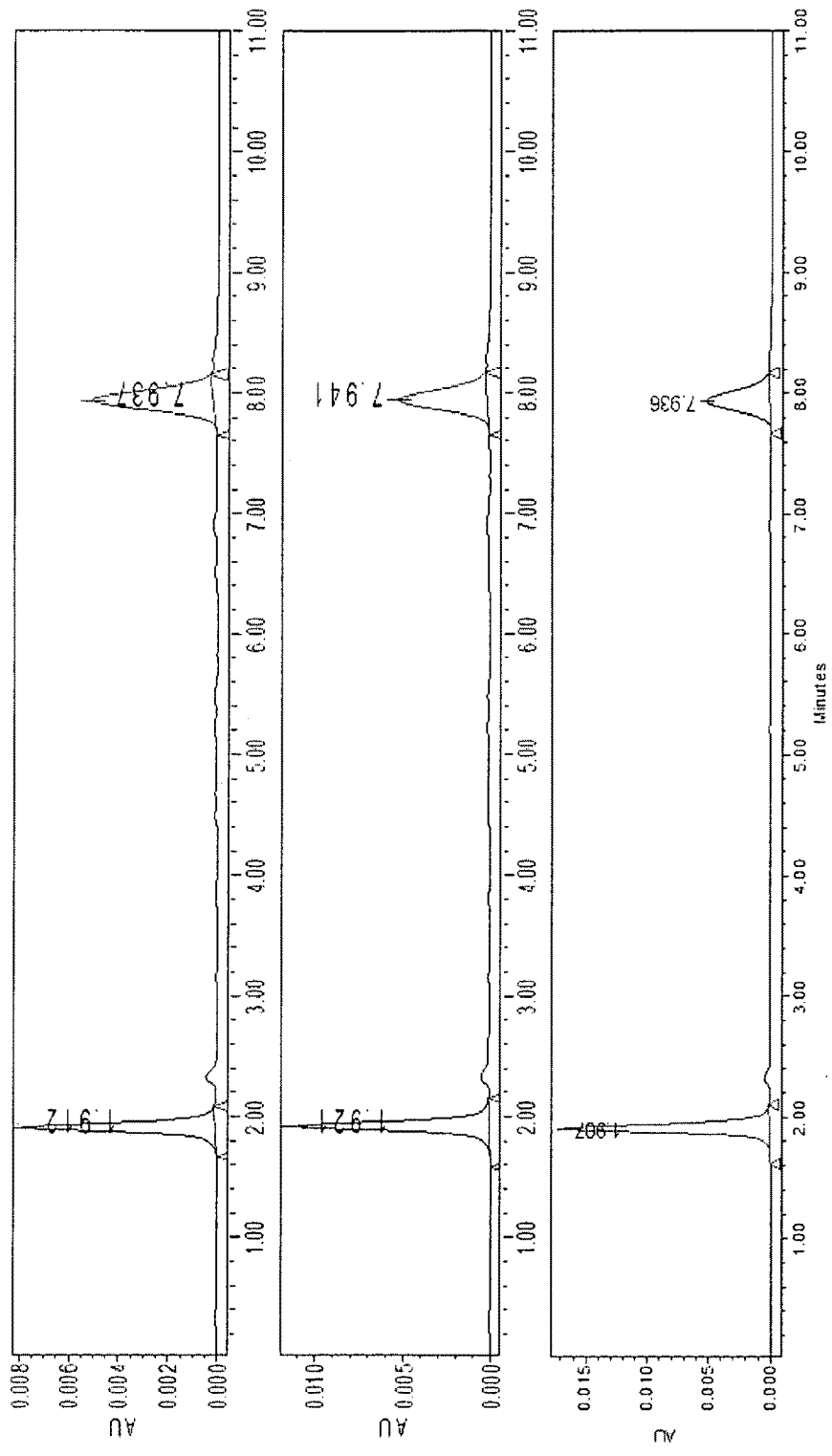
FIG. 9A shows charts depicting the characterization of JP-3-110 aqueous solution (0.4 mg/mL) stored in 4° C. for 1 week. The peak at 2 minutes was denoted as MPA degraded from JP-3-110. T NP does not have a benzene ring therefore cannot be detected under UV detector.
Figure 9B:
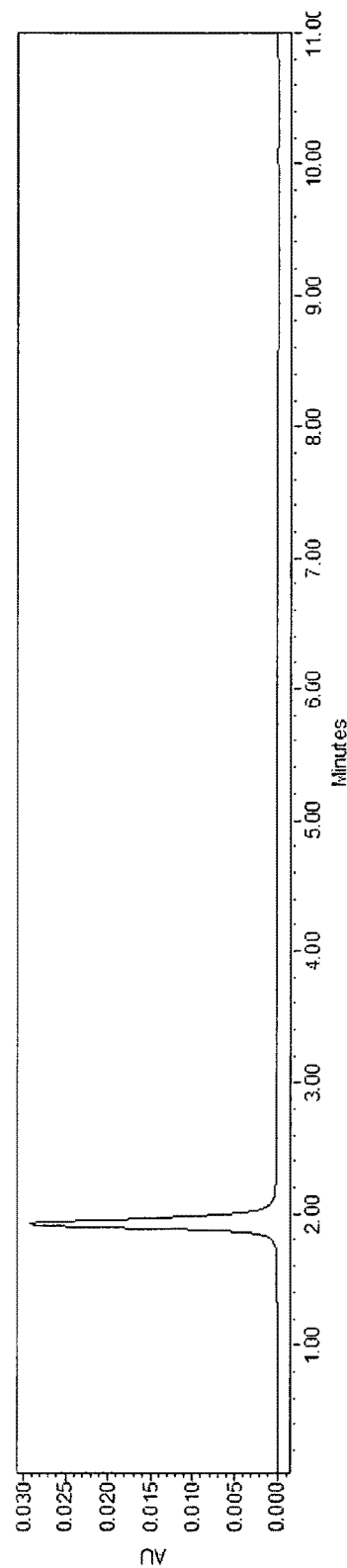
FIG. 9B shows a chart depicting the HPLC analysis of MPA under the same setting as above.

Quinic acid amide analog TNP was synthesized as described before. See Zeng et al., 2009, *Bioorganic & Medicinal Chemistry Letters*, 19:5458-5460. JP-3-110 was synthesized by conjugating TNP with MPA and the structure of JP-3-110 was confirmed by 1H NMR. FIG. 1B. The solubility of JP-3-110 was determined to be 0.48±0.16 mg/ml (0.80±0.27 mM) by HPLC, which is practically insoluble according to USP solubility criteria. FIGS. 7A-7D. To improve solubility, the inventors conceived to introduce aqueous solubility enhancing groups such as ionizable groups —CO$_2$H, —SO$_3$H or amino groups, sugars at positions R$_1$, R$_2$ and/or R$_{10}$ of Formulas II and III. Such introduction would require routine skills. The ester bond of JP-3-110 is susceptible to hydrolytic degradation, releasing TNP and MPA as two single drugs. More than 40% of JP-3-110 in the aqueous solution will be degraded when stored in 4° C. for 1 week (FIGS. 9A-9C).

JP-3-110 Suppressed the NF-κB Activity

Figure 2:
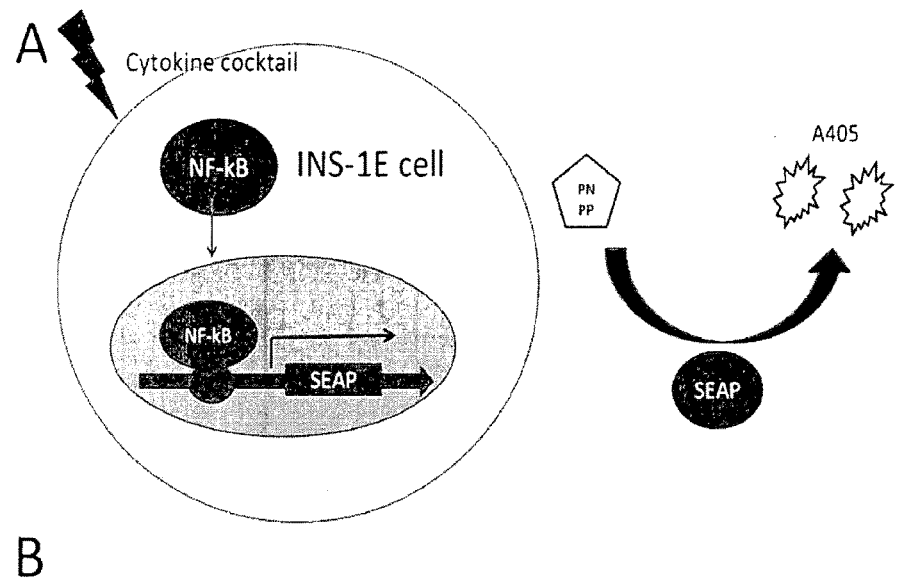
FIG. 2A shows a schematic illustration of the mechanism of SEAP reported gene assay to determine NF-kB activity. Briefly, a plasmid construct containing NF-kB promoter and SEAP gene was transferred into INS-1E cells by lipofectamine. SEAP was then expressed and secreted into culture supernatant and allowed chemiluminescent detection using a substrate PNPP under 405 nm.
FIG. 2B shows a chart depicting the supression of NF-κB activity by JP-3-110, TNP [(1S,3R,4S,5R)—N-butyl-1,3,4,5-tetrahydroxycyclohexane-1-carboxamide; Formula I, with R1=n-propyl; R2, R4, R6, R8=H; R3, R5, R7, R9=OH] and MPA in INS-1E cells. NF-kB activity was measured 24 hours after addition of cytokine cocktail (10 ng/mL TNFα, 5 ng/mL IL-1β and 10 ng/mL IFN-γ) alone or with JP-3-110 (5 μM) or TNP (5 μM) or MPA (5 μM). Blank, no cytokine stimulation. Cyt, cytokine cocktail. Results are presented as the mean±S.D., n=3.
Figure 2:
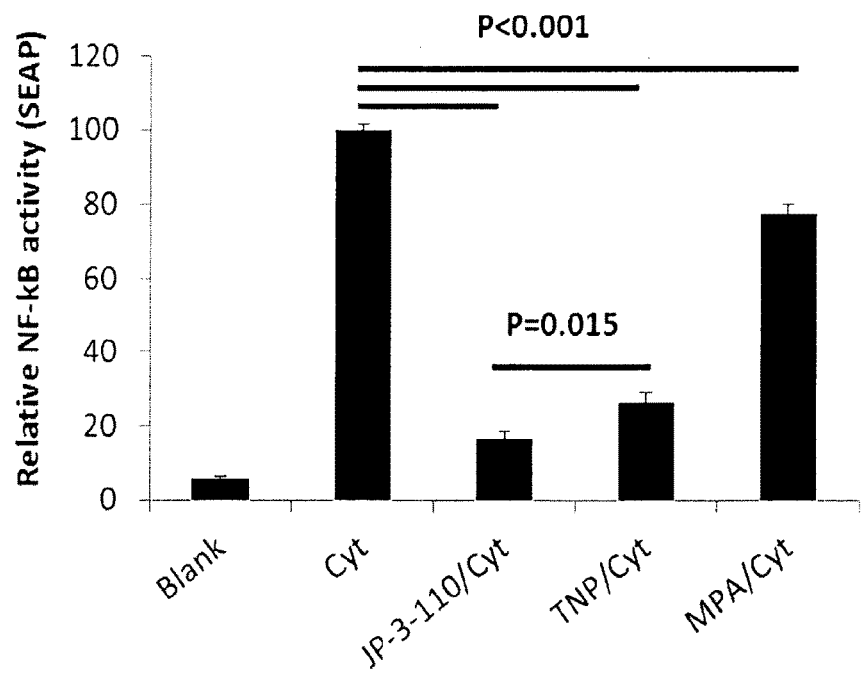

The inventors first tested whether JP-3-110 suppressed NF-κB activity in insulin-producing INS-1E cells which had been stably transfected with the SEAP gene containing the response-element for NF-κB. A cocktail of inflammatory cytokines (10 ng/mL TNFα, 5 ng/mL IL-1β and 10 ng/mL IFN-γ) was used to mimic the inflammation in vivo and activated the NF-κB activity. the inventors demonstrated that MPA, TNP and JP-3-110 at 504 significantly reduced the NF-κB activities in INS-1E cells (FIGS. 2A and 2B). Among three groups, JP-3-110 caused the most reduction in NF-κB activities, suggesting the synergistic anti-inflammatory effect of TNP and MPA.

JP-3-110 Exhibited a Similar Immunosuppressive Effect to that of MPA

Figure 3A:
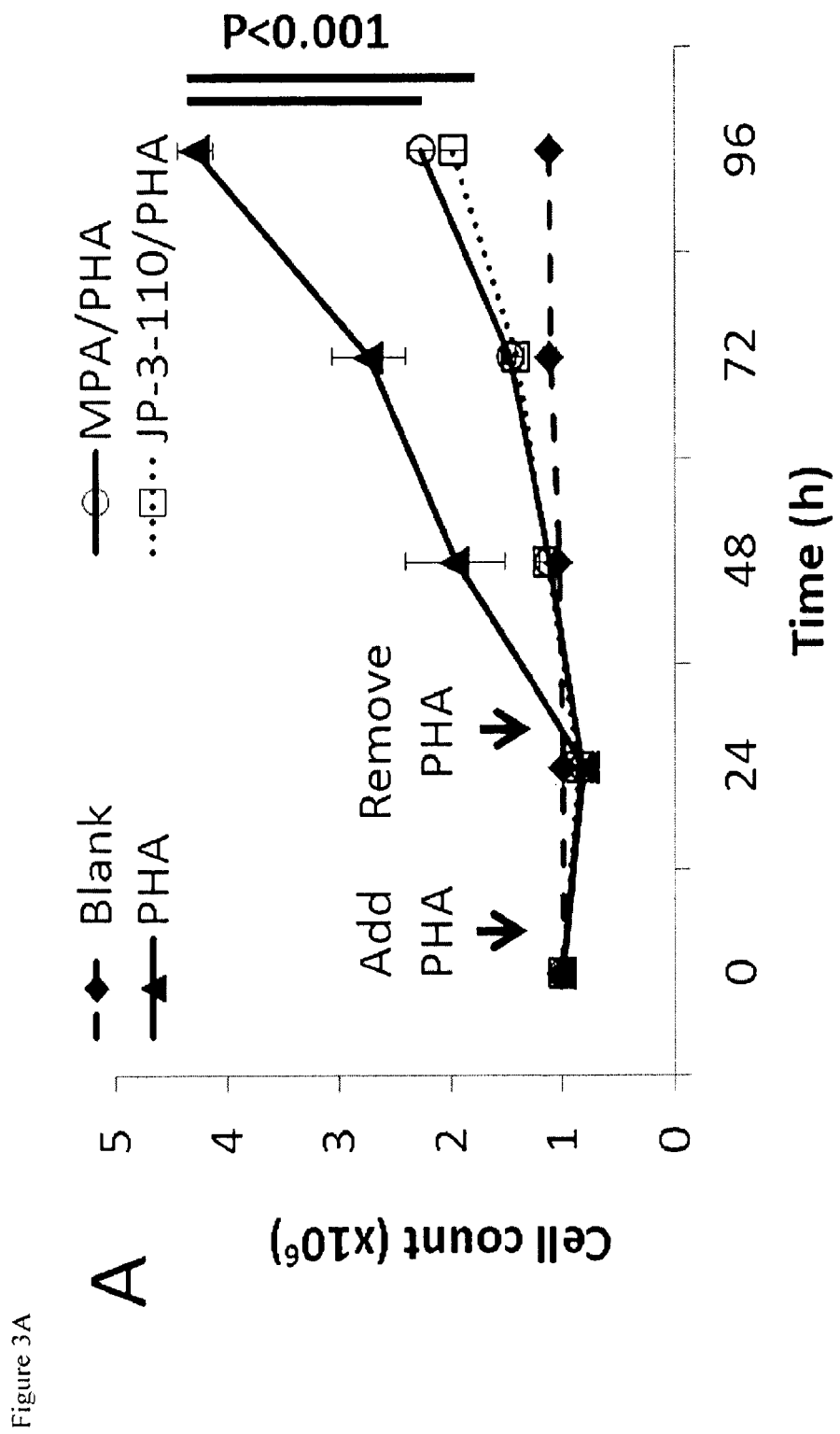
FIG. 3A shows a chart depicting the proliferative curve of the PHA-stimulated T cell under the treatment of JP-3-110 (5 μM) and MPA (5 μM). Briefly, human peripheral blood mononuclear cells PBMCs were isolated from human buffy coat using Ficoll-Paque. T cells (5×105) were isolated from PBMCs using dynabeads for human CD3+ T cells and subjected to PHA (1 μg/mL) stimulation for 24 h alone or with JP-3-110 (5 μM) and MPA (5 μM) for additional 48 h. The PHA-stimulated proliferation of T cells is characterized by a quick drop in the early stage (24 h) and a following fast-proliferative stage.
Figure 3B:
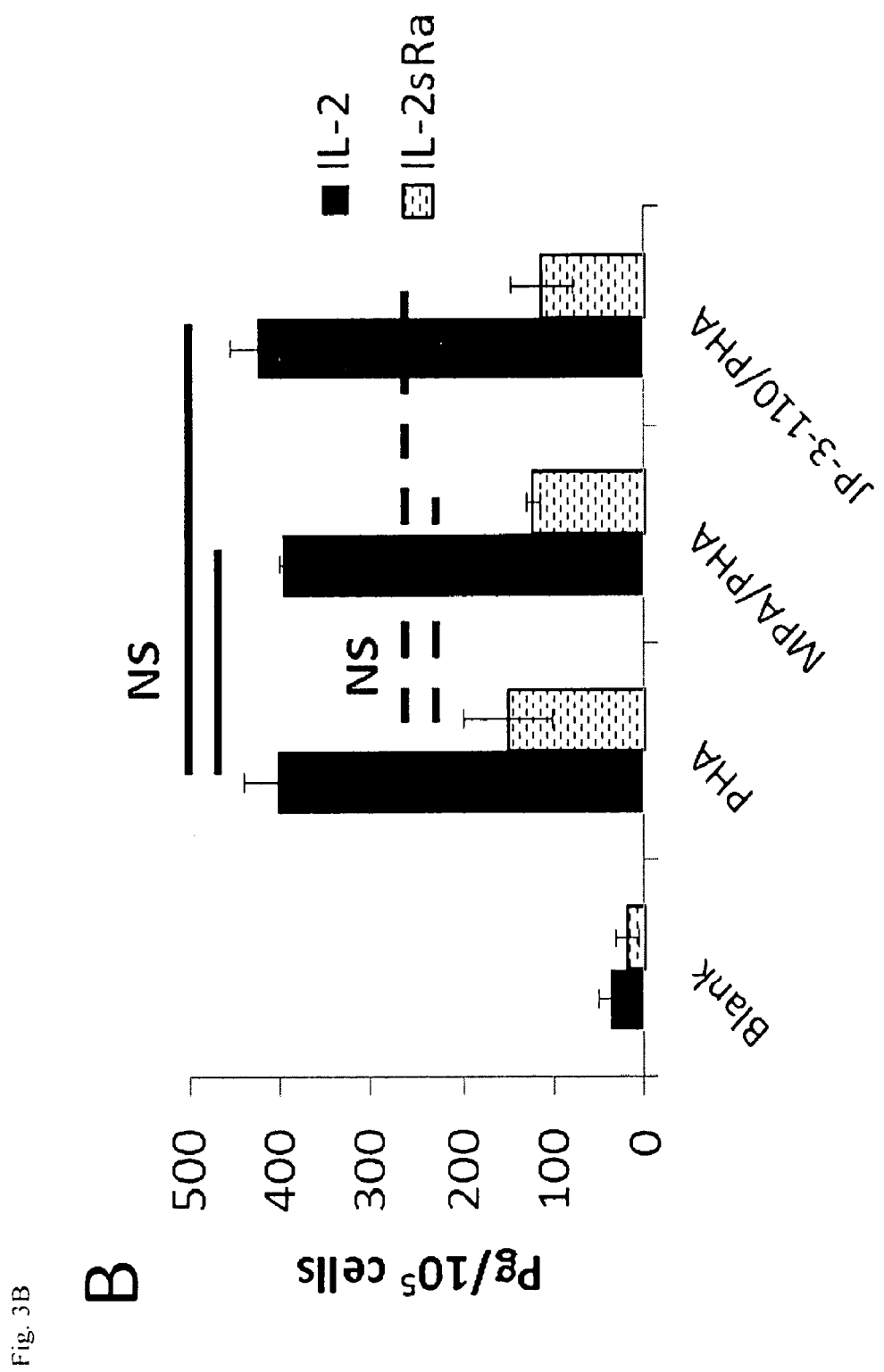
FIGS. 3B and 3C show charts depicting the levels of IL-2, IL-2 receptor, TNFα and IFNγ in the media of T cells at 48 h following PHA stimulation. IL-2 and IL-2 receptor were transient expressed markers for early stage T cell activation while TNFα and IFNγ were stably expressed markers for later-stage T cell activation. Results are presented as the mean±S.D., n=6.
Figure 3C:
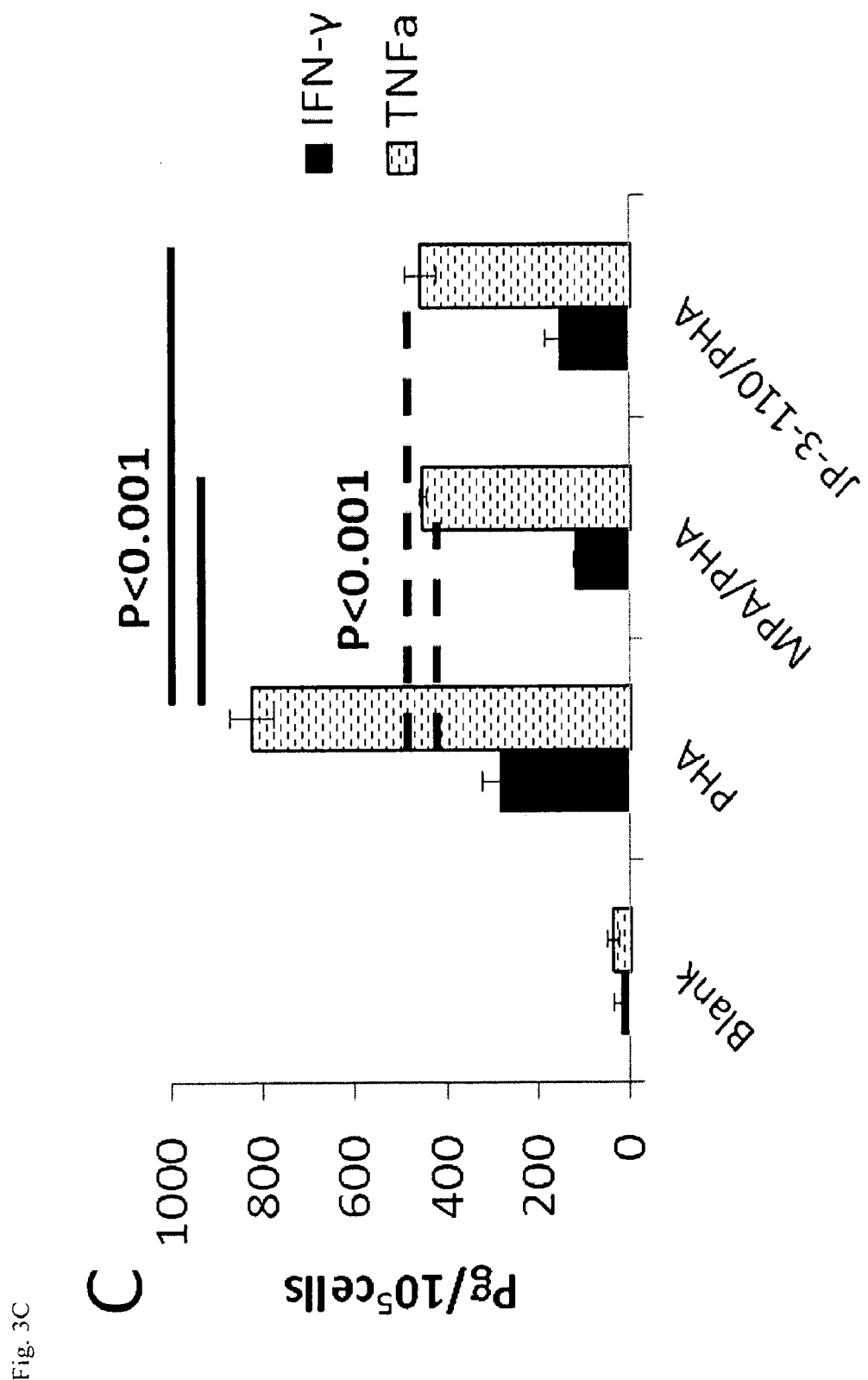
Figure 8A:
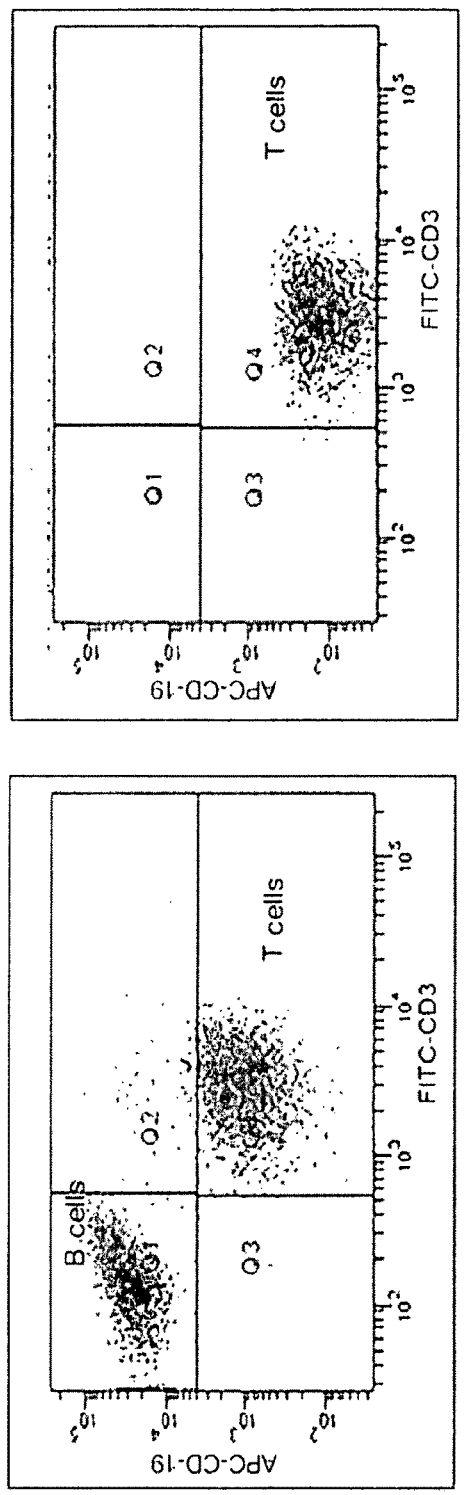
FIG. 8A shows flow cytometry results of isolated PBMCs (left) and CD3+ T cells (right) from fresh buffy coat.

Mixed lymphocytes reaction was used to determine the immunosuppressive effects of MPA and JP-3-110. T cells were purified using dynabeads from peripheral blood mononuclear cells (PBMCs), which were initially isolated from human buffy coat (FIG. 8A). The inventors did not observe any immunosuppressive effect of TNP (data not shown). Our results showed that JP-3-110 was equally potent as MPA to suppress the proliferation of T cells in 4 days (FIG. 3A). The levels of IL-2, IL-2sRa, TNFα and IFNγ were detected by ELISA to study the effects of JP-3-110 and MPA on T cell activation. IL-2 and IL-2R typically peaked at the first 48 h after PHA stimulation as markers for the early stage T cell activation, while TNFα and IFNγ were constitutively expressed by PHA-stimulated T cells as later-stage markers for T cell activation. JP-3-110 and MPA did not have any effect on the levels of IL-2 and IL-2 receptors (FIG. 3B), suggesting that JP-3-110 and MPA did not block the IL-2-dependent T cell proliferation. Surprisingly, JP-3-110 and MPA demonstrated moderate inhibition of the levels of TNFα and IFNγ (FIG. 3C). However, the results might be due to an overlap between the immunosuppressive pathway and the anti-inflammatory pathway of JP-3-110 and MPA. Taking together, the results indicated that JP-3-110 retained the similar immunosuppressive effect as MPA and that JP-3-110 suppressed the proliferation but not the activation of T cells.

JP-3-110 Suppressed the Function of T Cells and B Cells in Humanized NSG Mice

Figure 4:
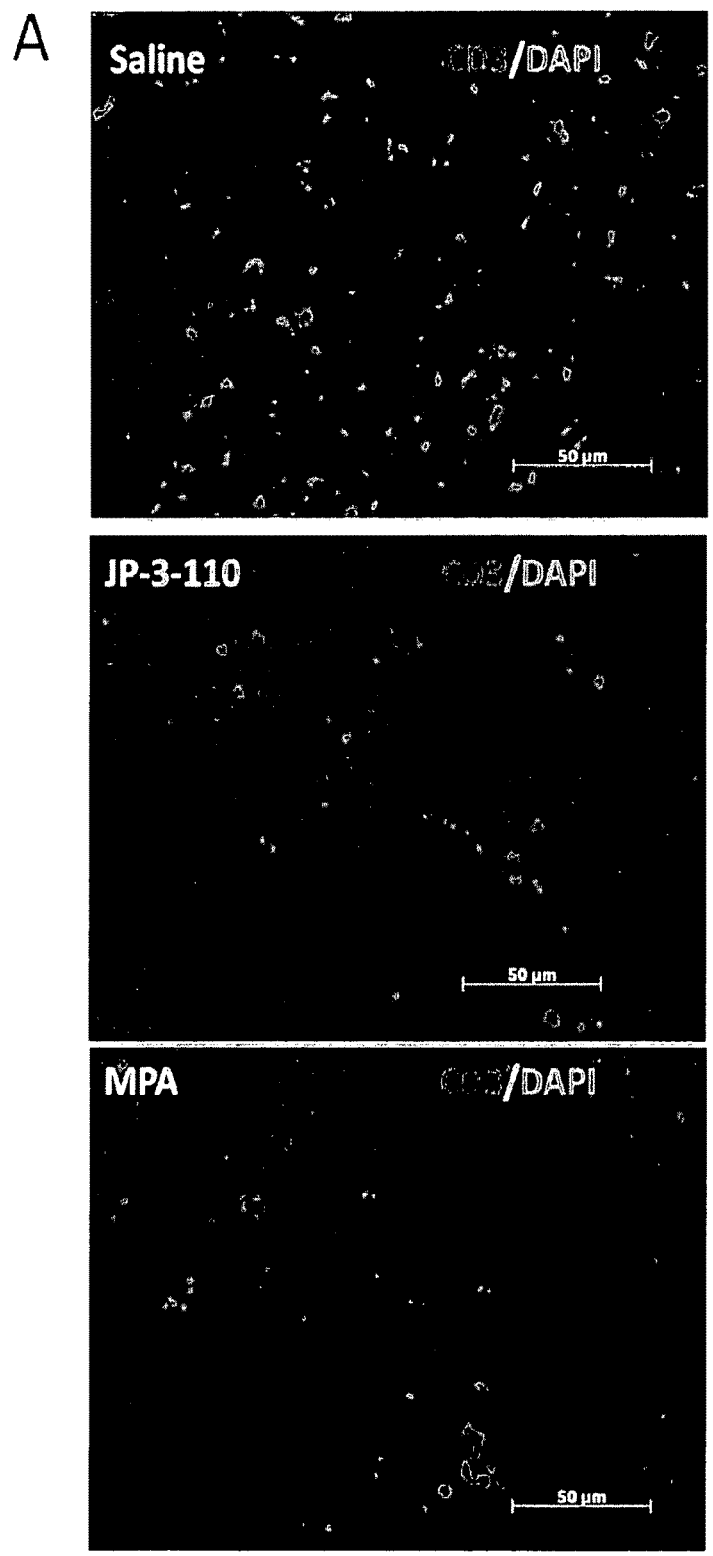
FIG. 4A shows photos depicting representative spleen sections of humanized NSG mice after receiving 7 consecutive shots of JP-3-110 (50 mg/kg, middle), MPA (50 mg/kg, lower) and equal amount of saline (upper), respectively. Human PBMCs (5×106/mouse) were injected intraperitoneally into NSG mice to introduce human immunity. Sections were stained to indicate human CD3+ T cells (red) and counterstained with DAPI (blue).
FIG. 4B shows a chart depicting the relative T cell intensity in the spleen sections of the above humanized NSG mice as quantified by ImageJ.
FIG. 4C shows a chart depicting the serum IgG levels of the above humanized NSG mice. Results are presented as the mean±S.D., n=5.
Figure 4B:
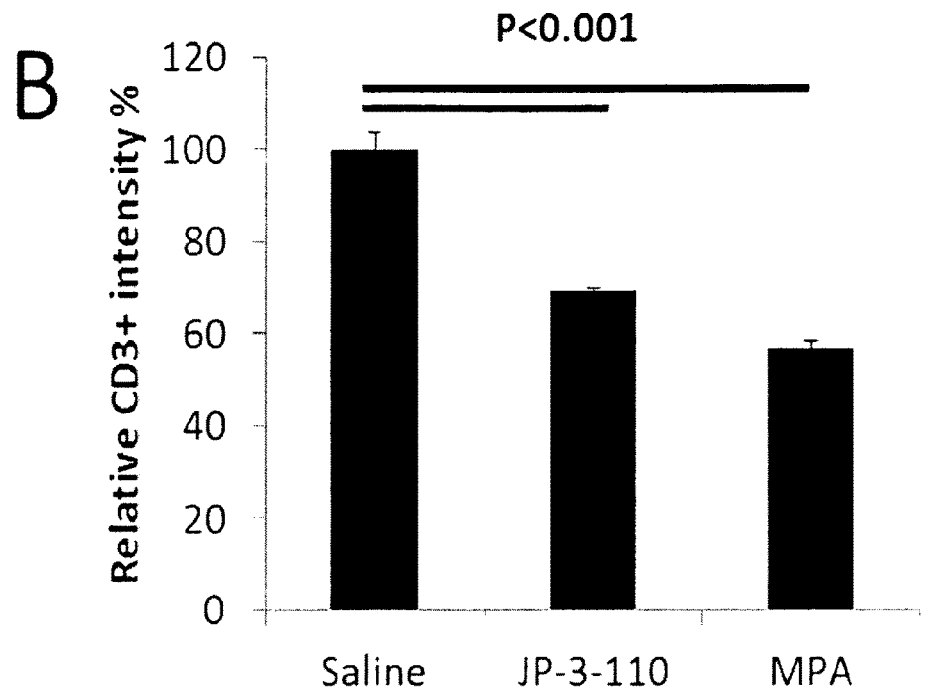
Figure 4C:
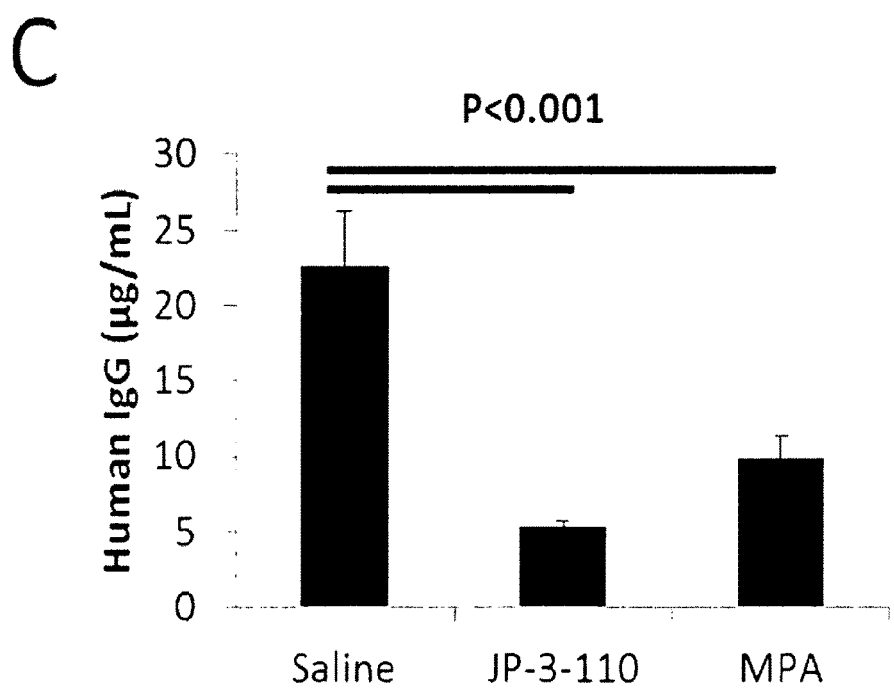
Figure 8B:
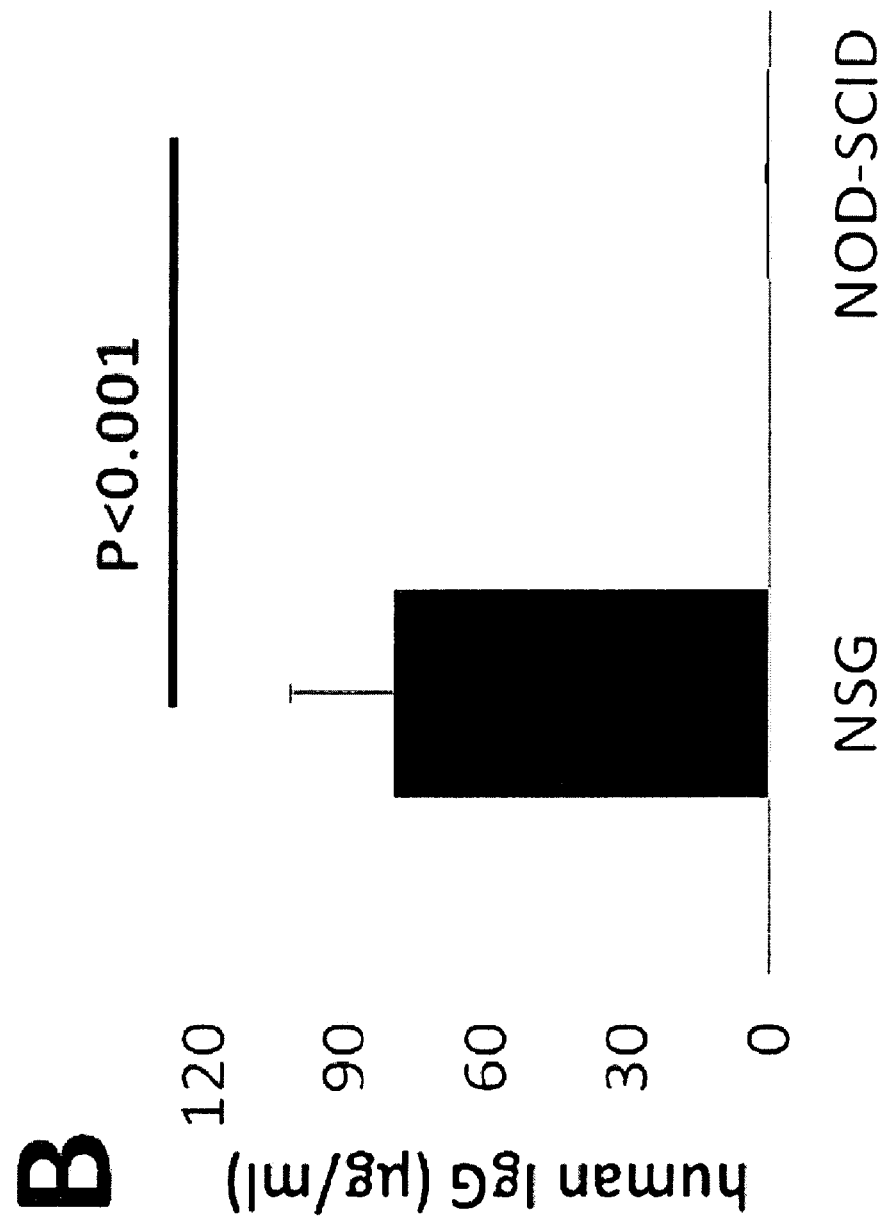
FIG. 8B shows a chart depicting the serum human IgG concentration in NSG mice and non-obese diabetic severe combined immunodeficient (NOD-SCID) mice at 2 weeks after the injection of PBMCs (5×106/mouse).
Figure 8C:
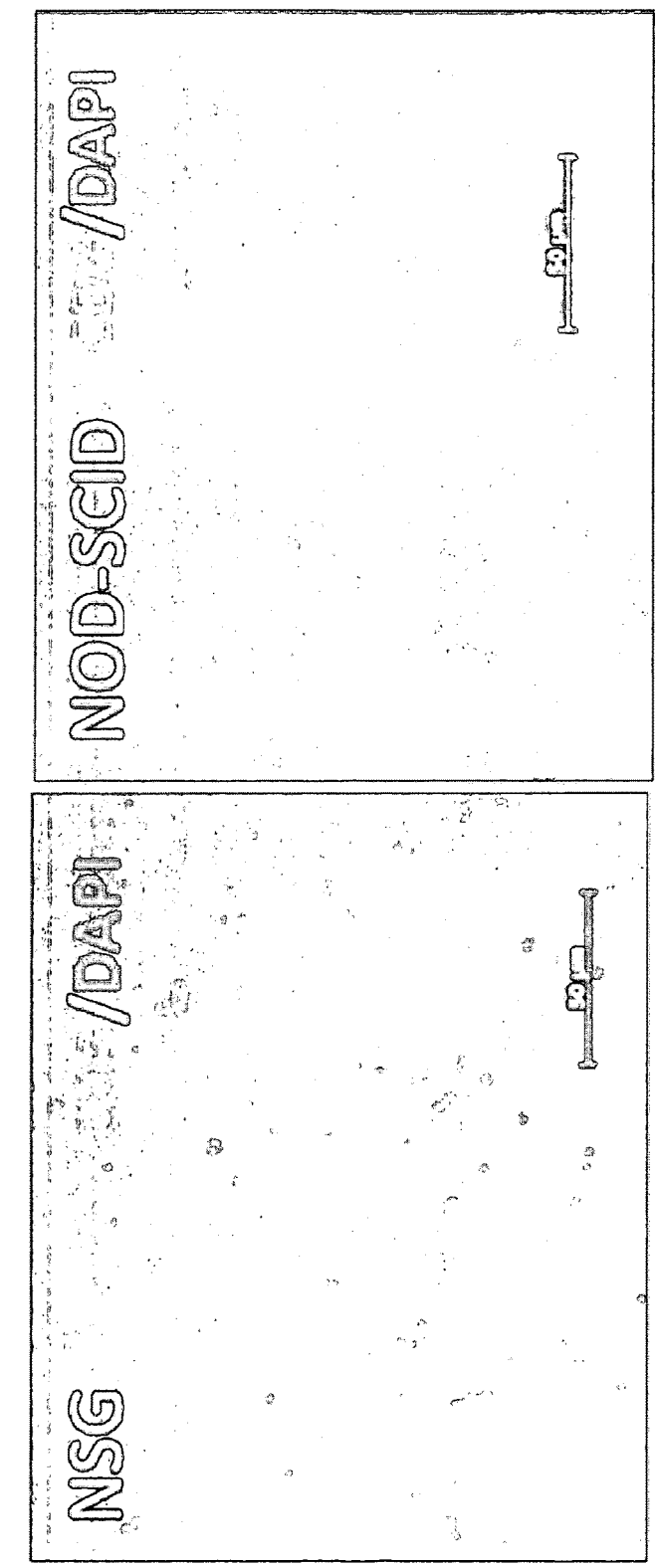
FIG. 8C shows photos depicting the staining of human CD3+ T cells in the spleen sections of NSG mice and non-obese diabetic severe combined immunodeficient (NOD-SCID) mice at 2 weeks after the injection of PBMCs (5×106/mouse).

To test the immunosuppressive effect of JP-3-110 in vivo, a humanized mouse model was used. Briefly, human PBMCs (5×10$^6$/mouse) were adoptively transferred into immunodeficient NSG mice to build human immunity. The human IgG level in the serum and human CD3+ T cell staining in the spleen was used to confirm the existence of human immunity (FIG. 8B). JP-3-110 and MPA was administrated intraperitoneally at 50 mg/kg for consecutive 7 shots. At the end of the study, the amount of human CD3+ T cells in the mouse spleen (FIGS. 4A-B) and the serum human IgG level (FIG. 4C) were significantly reduced in the mice receiving JP-3-110 and MPA administration compared with the mice receiving equal amount of saline, suggesting the immunosuppressive effect of JP-3-110. MPA showed slightly better immunosuppressive effect than JP-3-110 in humanized NSG mice, a result probably caused by the more molar amount of MPA injected into each NSG mouse.

JP-3-110 Showed Less Pro-apoptotic Effect than MPA

Figure 5A:
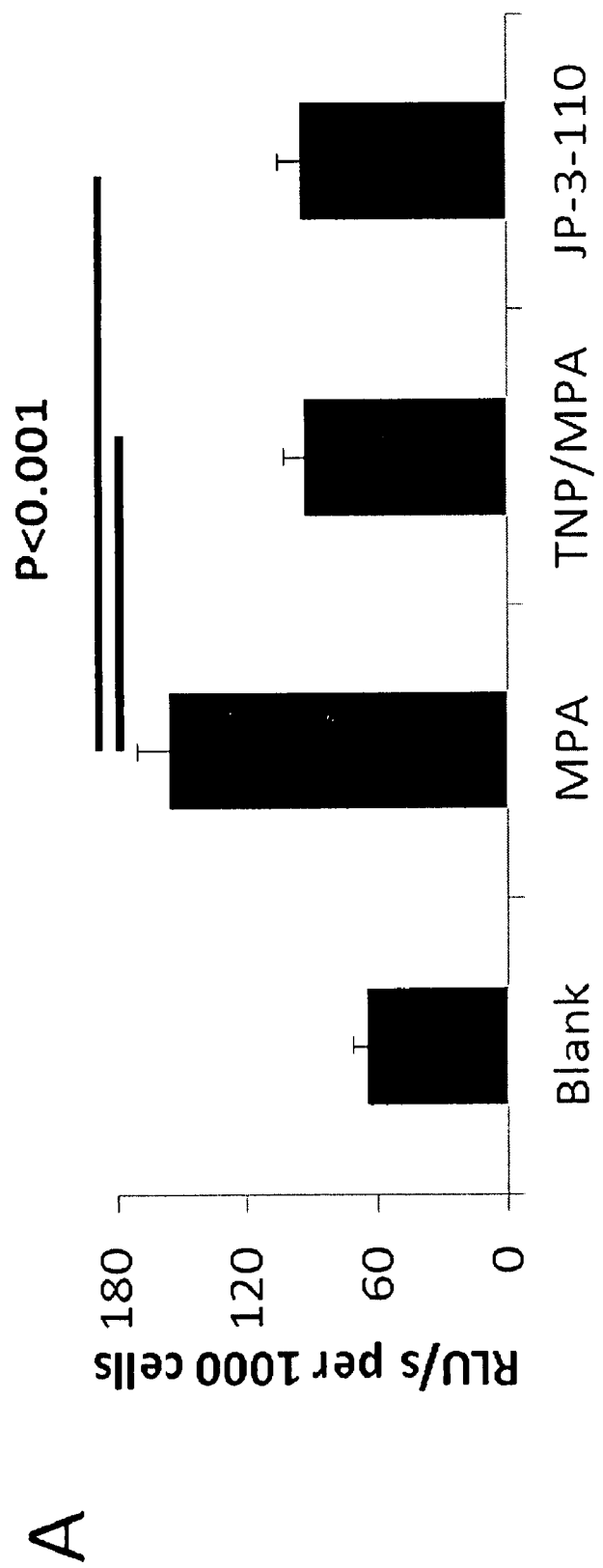
FIG. 5A shows a chart depicting caspase 3 activities in INS-1E cells after treated with MPA (20 μM), MPA+TNP (each of 20 μM) and JP-3-110 (20 μM) for 2 days. Results are presented as the mean±S.D., n=3.
Figure 5B:
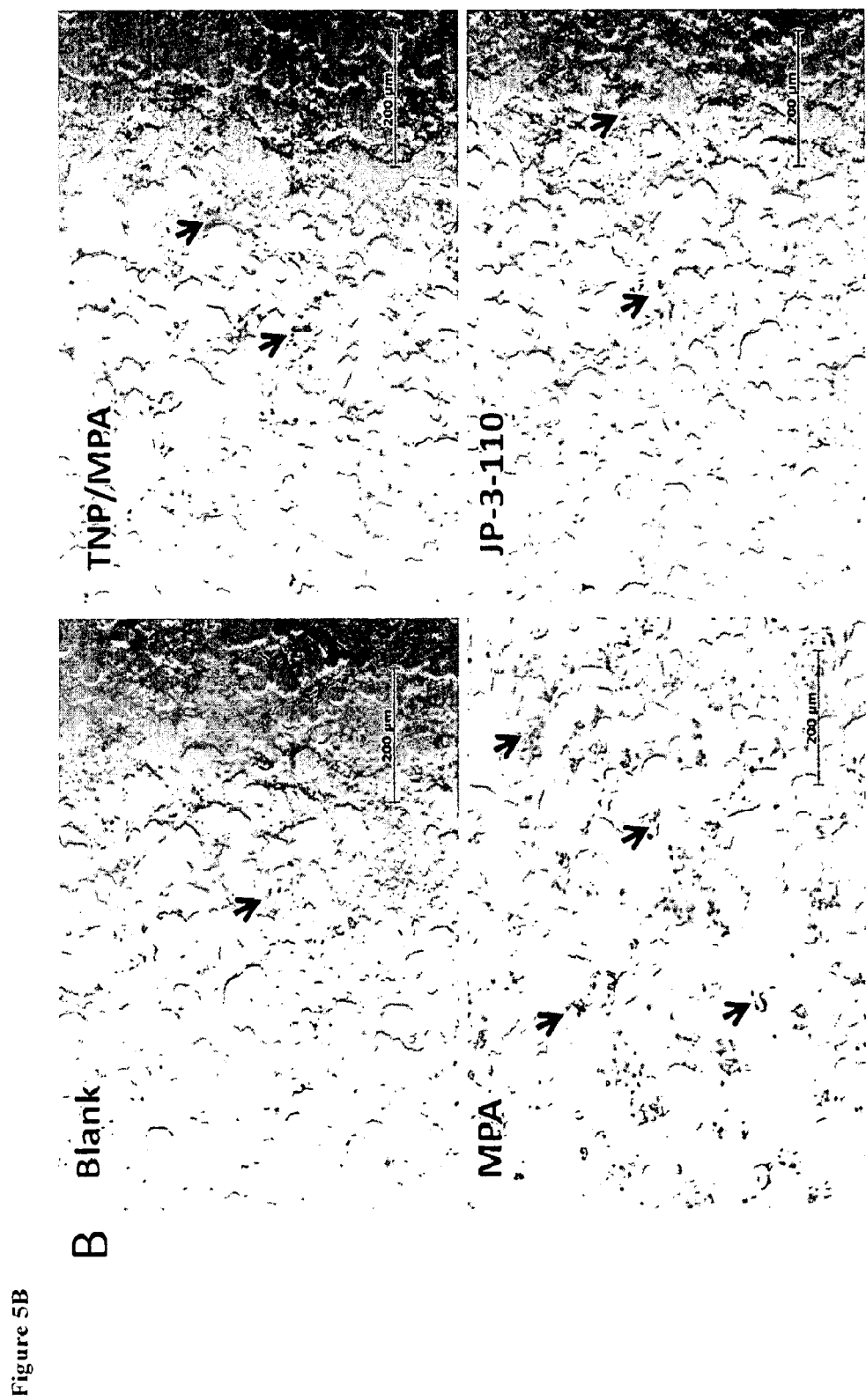
FIG. 5B shows photos depicting TUNEL assays of INS-1E cells as determined by DeadEnd Colorimetric TUNEL system. Apoptotic cells were stained in dark (arrows).
Figure 5C:
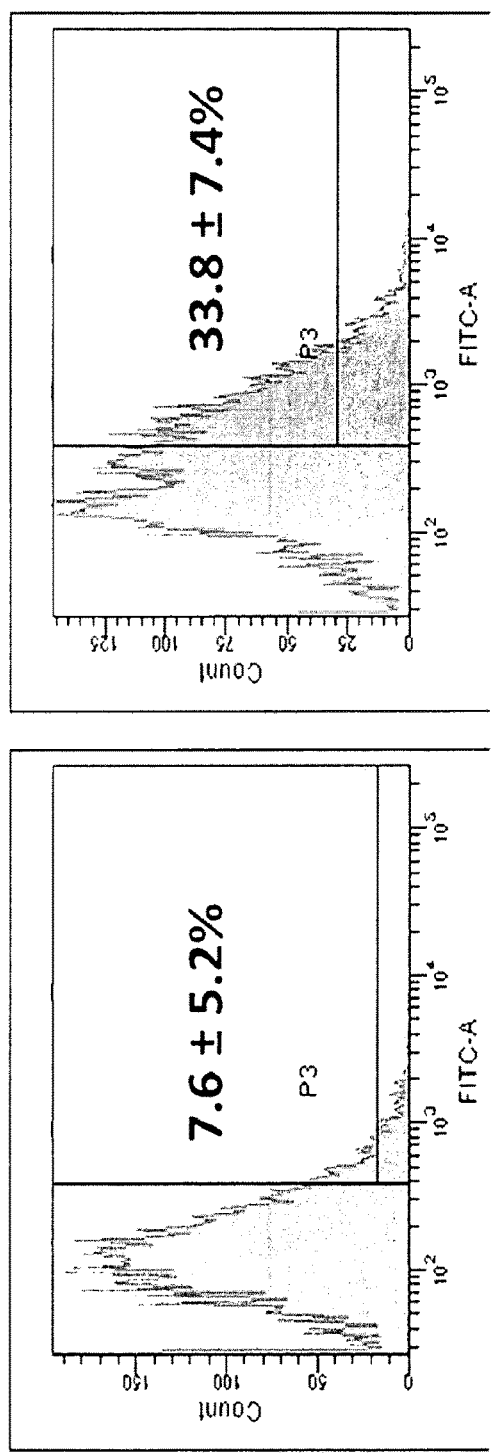
FIG. 5C shows charts depicting flow cytometry results of apoptotic cells that were stained with FITC labeled annexin V. Briefly, human islets were cultured with JP-3-110 (20 μM) or MPA (20 μM) for 5 days. Islet was collected and dispersed with 0.25% Trypsin/EDTA into single cell suspension. P3 indicated the percentage of apoptotic cells. All experiments were performed in triplicates. Results are presented as the mean±SD. *p<0.05 as determined by an unpaired Student's t-test, n=6.

We then determined the conjugation with TNP can reduce the pro-apoptotic effect of MPA. A relatively higher concentration (20 µM) of MPA was used to induce cytotoxicity. We first measured the caspase 3 activities of insulin-producing INS-1E cells under the stimulation of MPA alone, or MPA with free TNP, or JP-3-110 (MPA conjugated with TNP). Results showed that the presence of TNP in the media, whether in a free form or a conjugated form, effectively reversed the elevation of caspase 3 activity caused by MPA (FIG. 5A). TUNEL assay also suggested that the apoptotic cell death caused by MPA was effectively reversed by TNP, whether in a free form or a conjugated form (FIG. 5B). The inventors then determine the protective effect of TNP on human islets against MPA. MPA induced substantial apoptotic cell death in human islets after long-term coculture. However, the conjugated drug, JP-3-110 significantly reduced the percentage of apoptotic cells, suggesting less cytotoxicity to human islets than MPA (FIG. 5C). Therefore, JP-3-110 showed less cytotoxicity to INS-1E cells and human islets than MPA.

JP-3-110 does not Affect the Insulin Release of INS-1E Cells and Human Islets

Figure 6A:
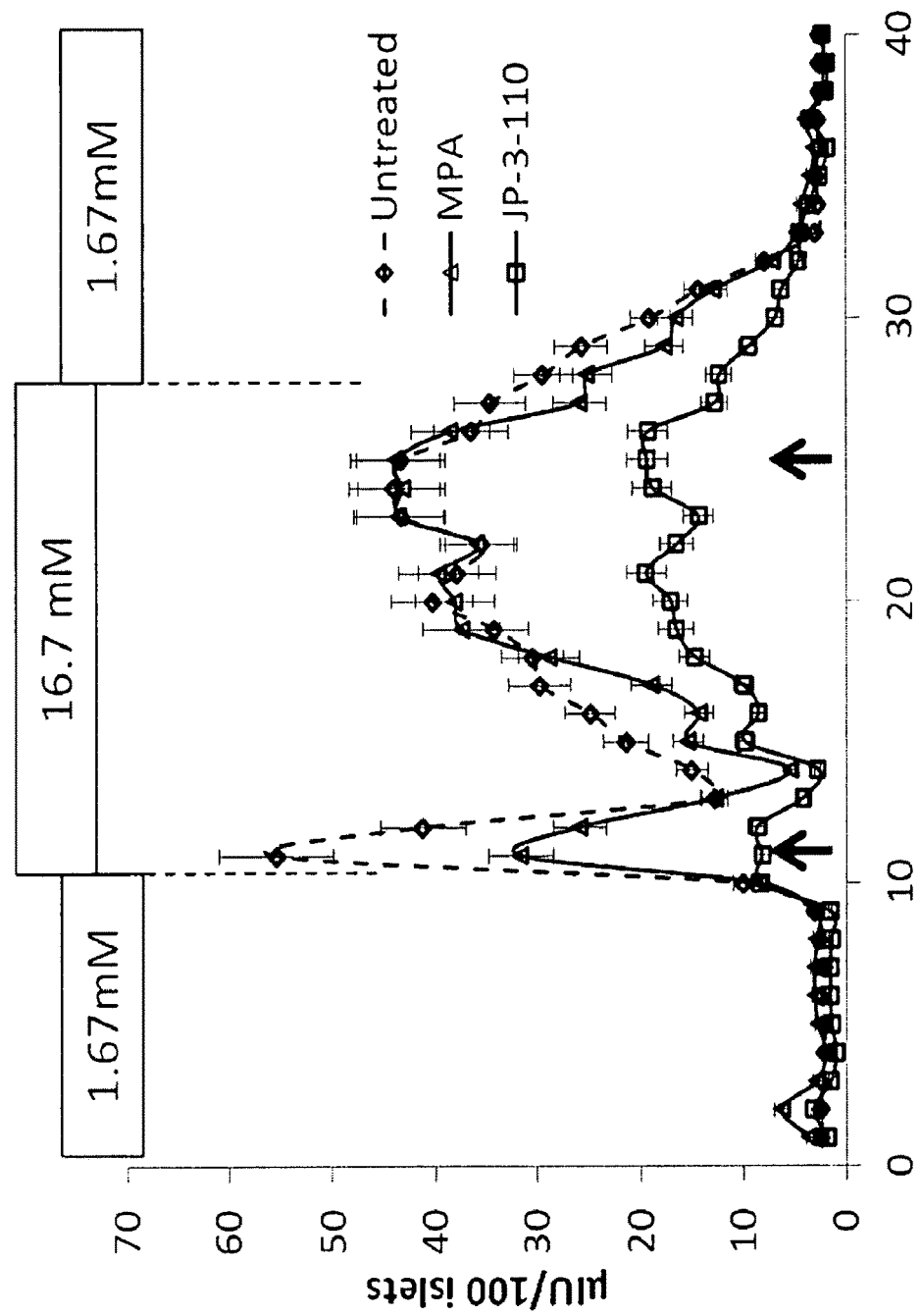
FIG. 6A shows a chart depicting the results of a dynamic insulin release assay that was used to determine the function of human islets. Briefly, 50 islets from each group were perifused with basal glucose for 60 min and stimulatory glucose for 30 min and finally with basal glucose until insulin release reversed to the basal level. Samples were collected through an automatic fraction collector and analyzed for insulin content by ELISA.
Figure 6B:
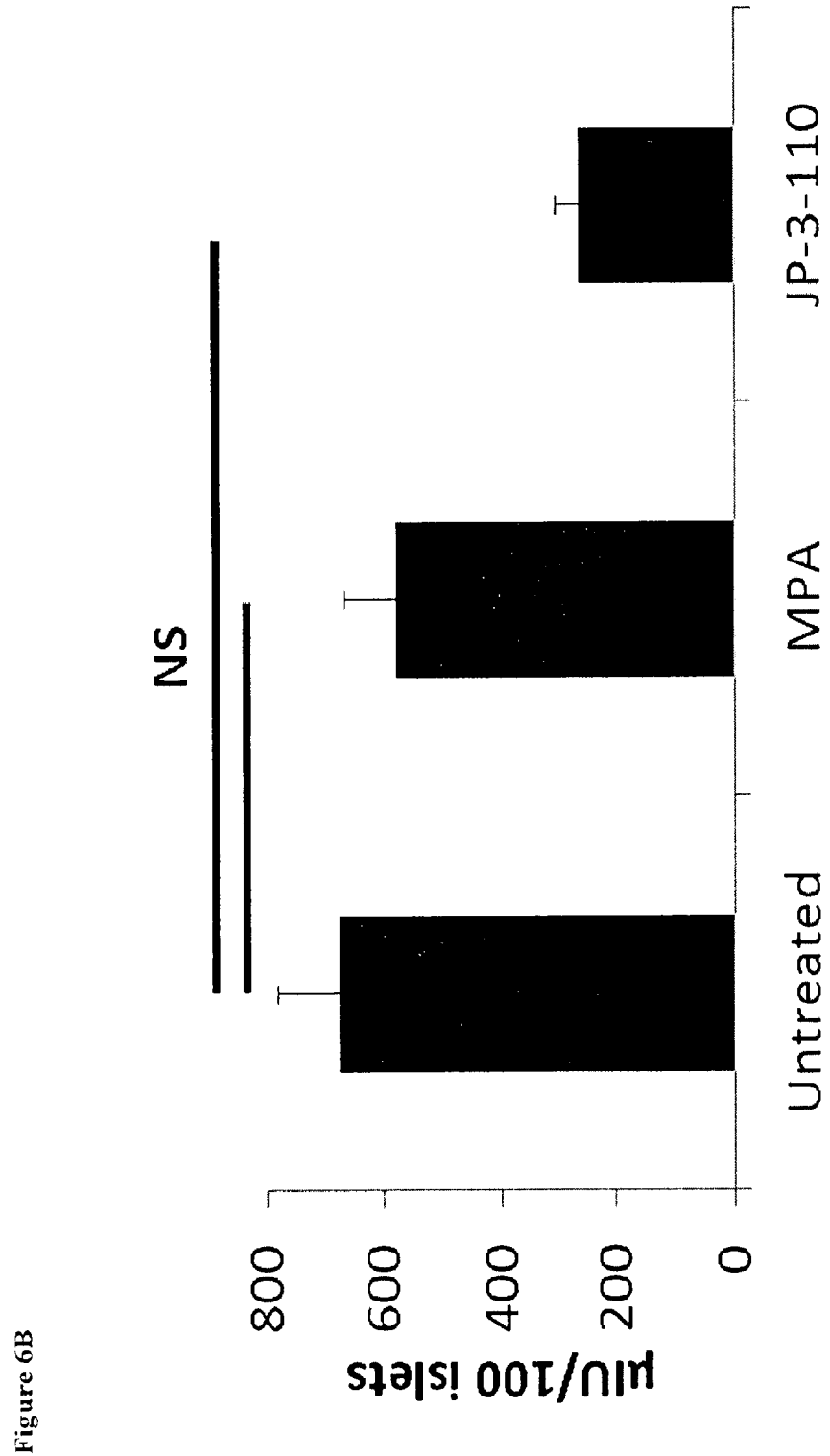
FIG. 6B shows a chart depicting the cumulative insulin release calculated according to FIG. 6B.
Figure 7B:
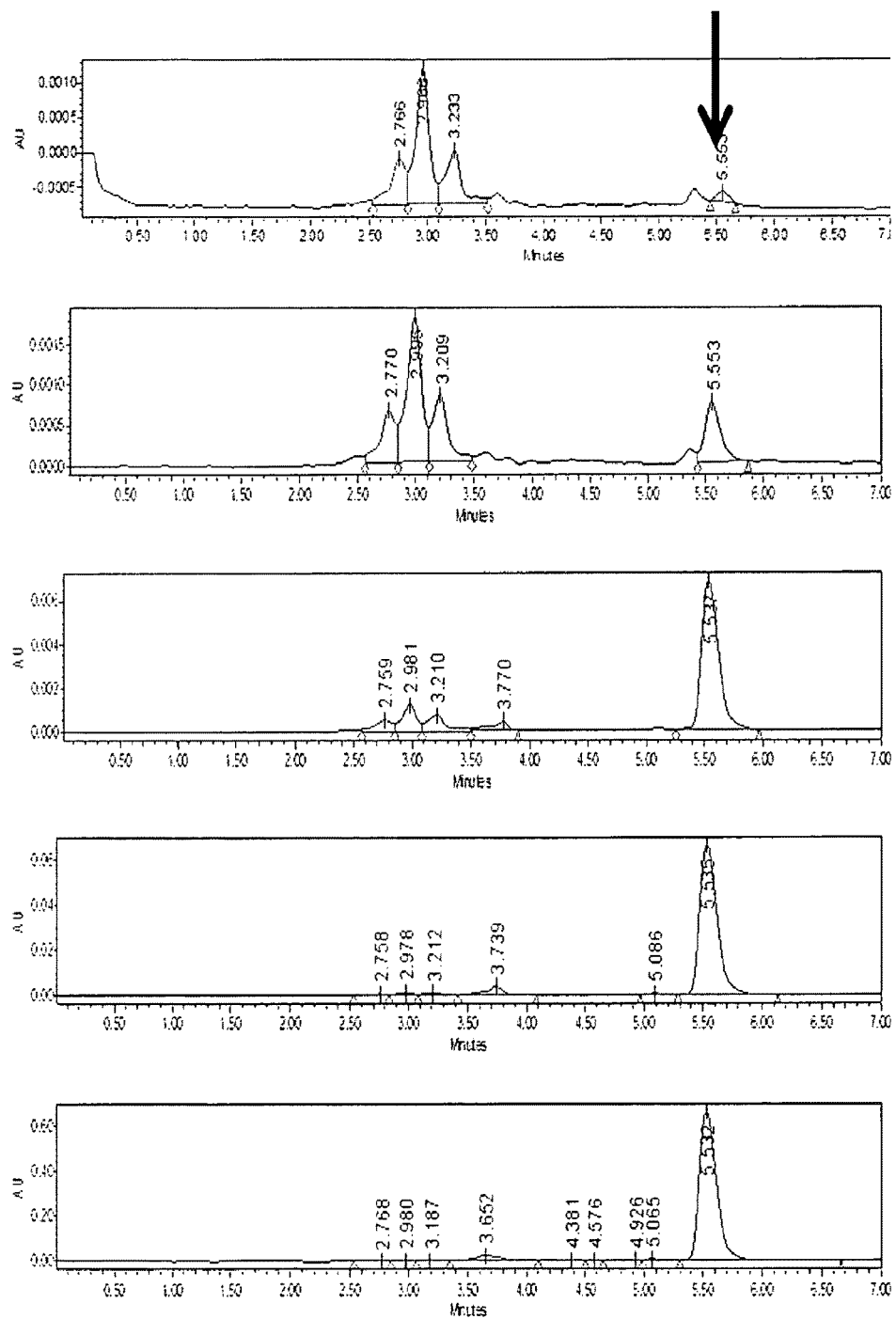
FIG. 7B shows charts depicting results of HPLC of JP-3-110 standards. From top to bottom, 0.2, 2, 20, 200, 2000 μg/mL of JP-3-110 in acetonitrile (ACN).
Figure 7C:
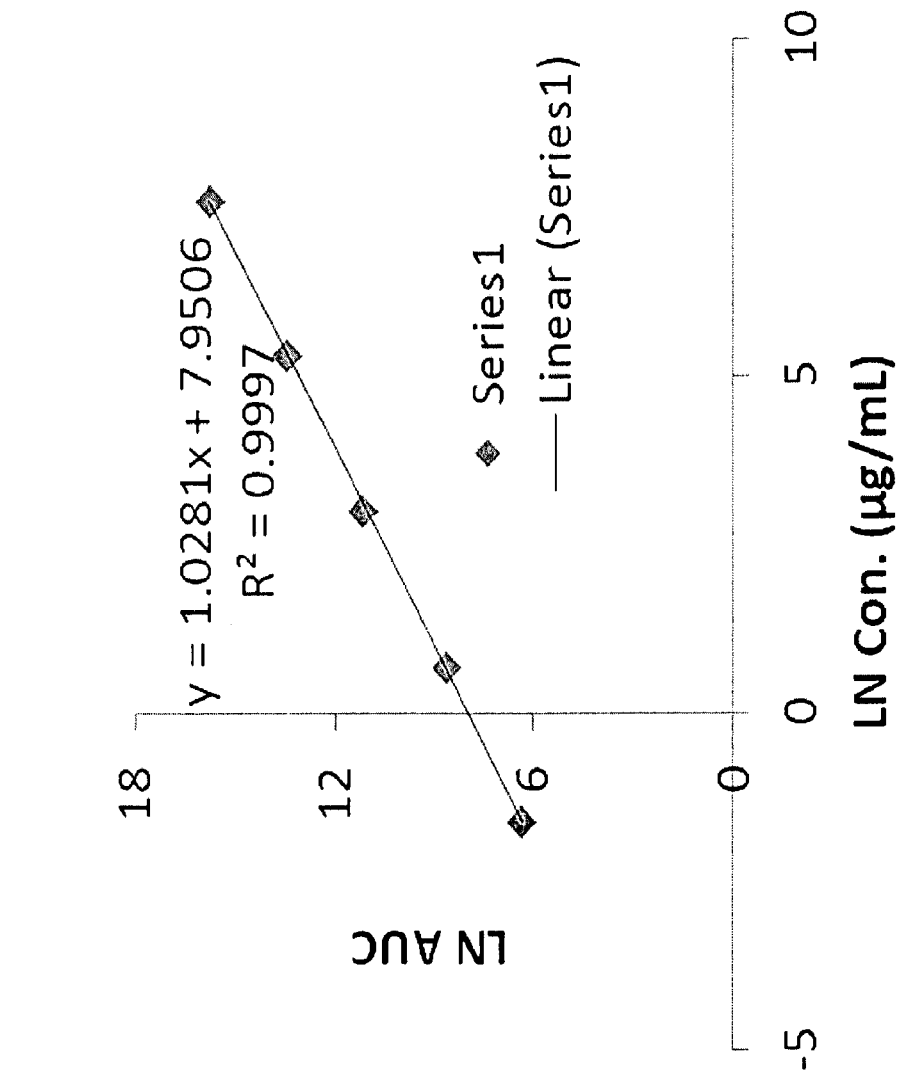
FIG. 7C shows a chart depicting the standard curve generated from the AUC of JP-3-110 standards.
Figure 7D:
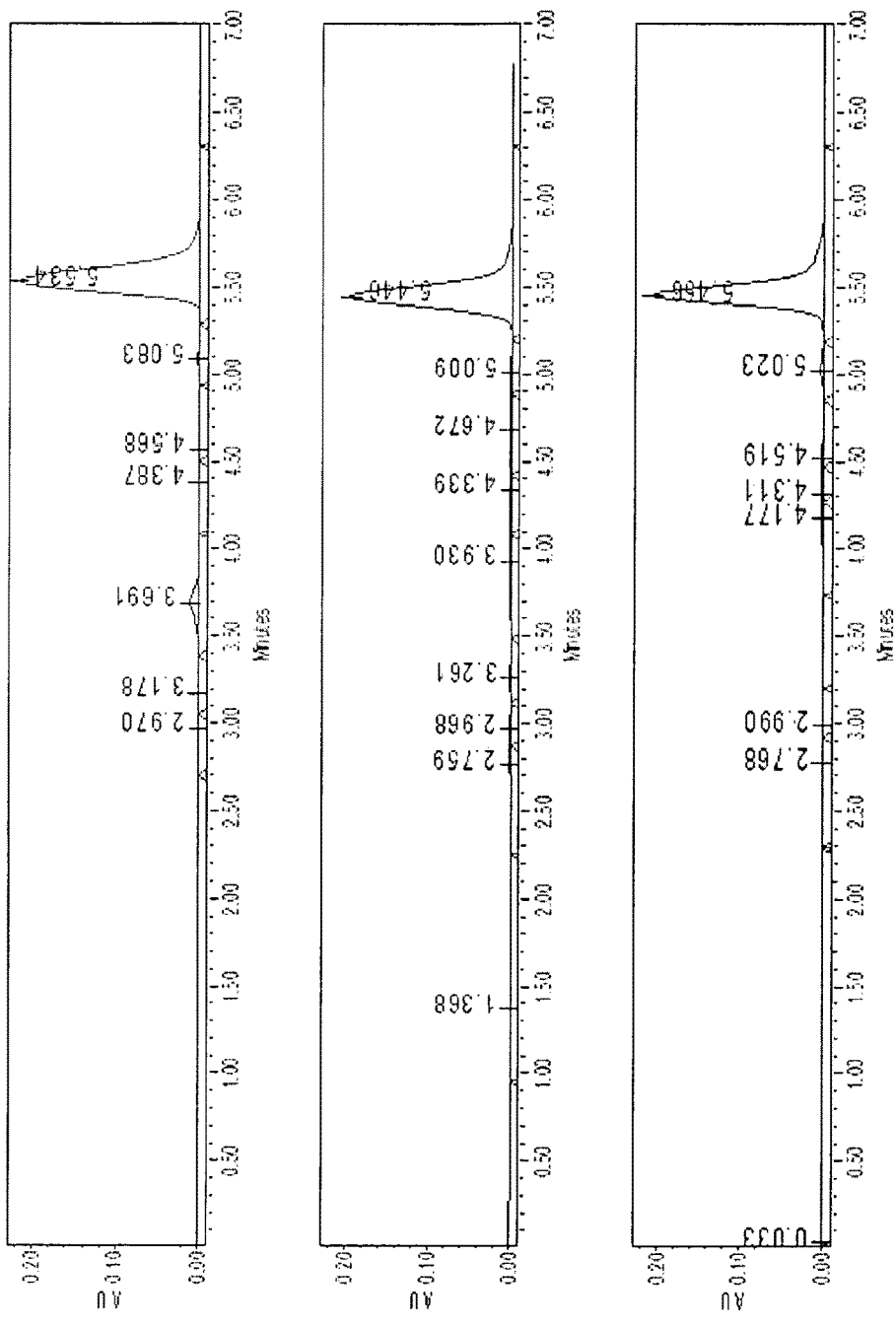
FIG. 7D shows charts depicting HPLC results of the triplicates of JP-3-110 saturated water solution.

A dynamic insulin release assay was used to evaluate the function of human islets. Briefly, 100 handpicked human islets were sequentially perfused with basal and stimulatory glucose. The samples were collected using an auto-sampler and subjected to ELISA. Fresh islets showed a typical biphasic pattern of insulin release under stimulatory glucose with a sharp and rapid release in the first two minutes and a long-lasting release afterward (FIG. 6A). The co-incubation with MPA impaired the insulin release from both phases and led to a significantly reduction in the total insulin release to stimulatory glucose (FIG. 6B). However, the JP-3-110 showed less toxicity to the insulin release as demonstrated by the clear biphasic insulin release.

While the present invention has been disclosed with reference to certain embodiments, numerous modifications, alterations, and changes to the described embodiments are possible without departing from the full scope of the invention, as described in the specification and claims.

What we claim are:

1. A method for improving survival and function of a transplanted tissue, comprising administering to the tissue a therapeutically-effective amount of a compound of Formula II or Formula III:

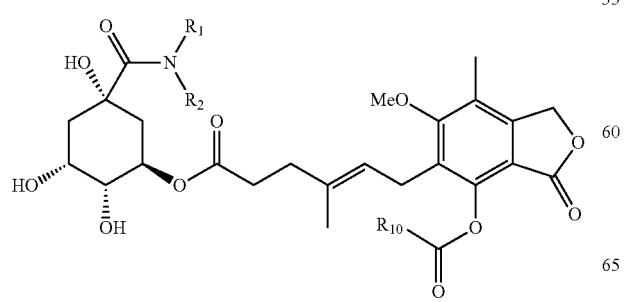

(II)

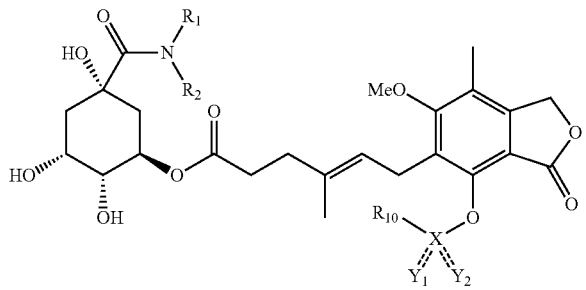

(III)

Wherein:
(i) X is S or P;
(ii) $Y_1$ and $Y_2$ are each independently O or N; and
(iii) $R_1$, $R_2$ and $R_{10}$ are each independently selected from the group consisting of:
 a) H or OH;
 b) a straight- and branched-chain alkyl having one to twelve carbon atoms;
 c) an alkylidene that is a divalent radical having one to twelve carbon atoms;
 d) an alkenyl that is straight- and branched-chain alkenyl groups having from two to twelve carbon atoms;
 e) an alkynyl that is straight- and branched-chain alkynyl groups having from two to twelve carbon atoms;
 f) a cycloalkyl that is saturated or partially unsaturated carbocycles having from three to twelve carbon atoms, including bicyclic and tricyclic cycloalkyl structures;
 g) a heterocycloalkyl that is a saturated or partially unsaturated monocyclic radical containing carbon atoms, preferably with 4 or 5 ring carbon atoms, and with at least one heteroatom selected from nitrogen, oxygen (e.g., monosaccharide) and sulfur;
 h) an aryl or heteroaryl that have monocyclic and polycyclic unsaturated or aromatic ring structures, with "aryl" referring to those that are carbocycles and "heteroaryl" referring to those that are heterocycles;
 i) an alkoxy that is a radical —O-alkyl;
 j) an aryloxy;
 k) a cycloalkoxyl;
 l) an alkylthio;
 m) an alkylamino;
 n) an arylthio;
 o) an arylamino;
 p) a cycloalkylthio;
 q) a cycloalkylamino;
 r) a heteroarylthio;
 s) a heteroarylamino;
 t) a halogen;
wherein every member in each group can be taken independently or combined via covalent bond in any order with some or all members of any group defined above to the extent that these combinations give rise to chemically feasible entities; and
wherein each of the groups 'b' through 's' can contain or be substituted by any one or more functional groups taken from the functional group pool listed below either singularly, in plurality or in combination with other members of the functional group, which functional group pool is consisting of ether, thioether, amine, nitro, nitrile, sulfoxides, sulfones, ester, amide, hydroxamic acid, sulfonamides, sulfamide, ureas, sulfimines, sulfonylureas, carbamates, thiocarbamates, carbonates and hydroxyl.

2. The method of claim 1, wherein the alkyl is selected from the group consisting of methyl (Me), ethyl (Et), n-propyl, isopropyl, butyl, isobutyl, sec-butyl, tert-butyl (t-Bu), pentyl, isopentyl, tert-pentyl, hexyl, and isohexyl.

3. The method of claim 1, wherein the alkyl is an alkyl having from 1 to 8 carbon atoms.

4. The method of claim 1, wherein the alkyl is a substituted alkyl selected from the group consisting of fluoromethyl, difluoromethyl, trifluoromethyl, 2-fluoroethyl, 3-fluoropropyl, hydroxymethyl, 2-hydroxyethyl, and 3-hydroxypropyl.

5. The method of claim 1, wherein the alkylidene is selected from the group consisting of $CH_2$, $CHCH_3$, and $(CH_3)_2$.

6. The method of claim 1, wherein the alkenyl is selected from the group consisting of prop-2-enyl, but-3-enyl, hex-3-enyl, 2-methylprop-2-enyl, and hept-2-enyl.

7. The method of claim 1, wherein the cycloalkyl is selected from the group consisting of cyclopropyl, cyclobutyl, cyclopentyl, cyclohexyl, and cycloheptyl.

8. The method of claim 1, wherein the aromatic ring structures in the aryl or heteroaryl is selected from the group consisting of phenyl, naphthyl, 1,2,3,4-tetrahydronaphthyl, furyl, thienyl, pyrrolyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and a fused-ring structure or bridge.

9. The method of claim 8, wherein a fused-ring structure or bridge is $OCH_2$.

10. The method of claim 1, wherein the alkoxy is selected from the group consisting of methoxy, ethoxy, propoxy.

11. The method of claim 1, wherein the halogen is selected from the group consisting of chlorine, fluorine, bromine and iodine.

12. The method of claim 1, wherein Formula II refers to a compound of Formula IV

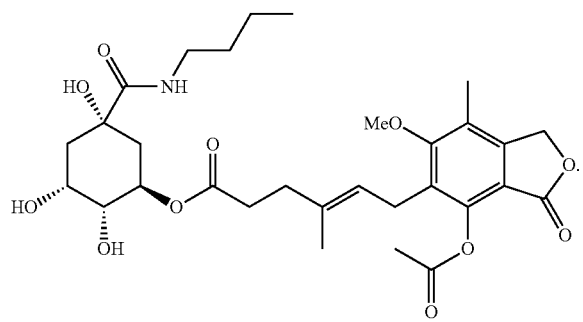

(IV)

13. The method of claim 12, wherein the compound of Formula IV is in a mono or di salt form.

14. The method of claim 1, wherein Formula III refers to a compound of Formula V

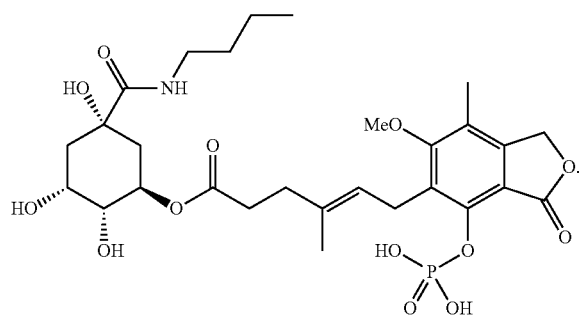

(V)

15. The method of claim 14, wherein the compound of Formula V is in a mono or di salt form.

* * * * *